United States Patent [19]

Heine et al.

[11] Patent Number: 4,529,813
[45] Date of Patent: Jul. 16, 1985

[54] PRODUCTION OF INSECTICIDALLY ACTIVE VINYL-CYCLOPROPANE CARBOXYLIC ACID ESTERS

[75] Inventors: Hans-Georg Heine; Willy Hartmann, both of Krefeld, Fed. Rep. of Germany

[73] Assignee: Bayer Aktiengesellschaft, Leverkusen, Fed. Rep. of Germany

[21] Appl. No.: 130,506

[22] Filed: Mar. 14, 1980

Related U.S. Application Data

[62] Division of Ser. No. 827,514, Aug. 24, 1977, abandoned.

[51] Int. Cl.³ .................... C07C 69/74; C07C 69/02; C07C 67/02
[52] U.S. Cl. .................................. 560/123; 560/231; 560/250; 564/188; 564/191; 564/123; 260/464; 260/465 D; 260/465 E; 260/465 H; 260/465 G; 568/305; 568/306; 568/323; 568/329; 568/330; 568/364; 568/365; 568/381
[58] Field of Search ............... 568/381, 364, 305, 306, 568/323, 329, 330, 365; 560/123, 231, 250; 564/188, 191, 123; 260/464, 465 D, 465 E, 465 H, 465 G

[56] References Cited

U.S. PATENT DOCUMENTS 4,064,174 12/1977 Verbrugge .......................... 562/506
4,242,278 12/1980 Martin et al. ...................... 562/506

OTHER PUBLICATIONS

"Synthetic Org. Chem.", Wagner & Zook (1965), pp. 98, 99, 100, 101.

*Primary Examiner*—Alan Siegel
*Attorney, Agent, or Firm*—Sprung Horn Kramer & Woods

[57] ABSTRACT

Insecticidally active vinyl-cyclopropane carboxylic acid esters of the formula

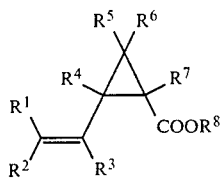

are prepared by reacting

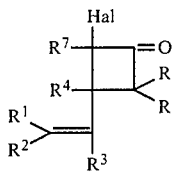 or 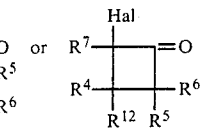

(II)          (V)

in which
$R^{12}$ is a radical selected from the group consisting of

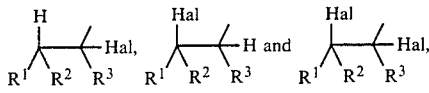

with an alcoholate of the formula $M-O-R^8$.

Various processes for making the intermediates are also described. Many of the intermediates and end products are new.

1 Claim, No Drawings

PRODUCTION OF INSECTICIDALLY ACTIVE VINYL-CYCLOPROPANE CARBOXYLIC ACID ESTERS

This is a division of application Ser. No. 827,514, filed Aug. 24, 1977, now abandoned.

The present invention relates to an unobvious process for the preparation of certain vinyl-substituted cyclopropanecarboxylic acid esters, some of which are known, which can be used as intermediates for the preparation of insecticidally active compounds or which can be used themselves as insecticides.

The present invention also relates to certain new vinyl-substituted cyclopropanecarboxylic acid esters as well as to intermediates for their preparation.

Various chrysanthemumic acid esters, for example the pyrethrins, jasmolins or cinerins, are naturally occurring cyclopropanecarboxylic acid esters having an insecticidal action. They possess valuable properties which, however, are impaired by, for example, easy oxidative degradation. Synthetic products have also been found, for example m-phenoxybenzyl or 5-benzyl-3-furylmethyl esters of 2,2-dimethyl-3-(β,β-dihalogenovinyl)-cyclopropanecarboxylic acids, the insecticidal activity of which is said to be higher than that of the corresponding chrysanthemumic acid esters. In addition, the synthetic products are said to have a higher stability towards oxidative degradation (Nature 244, 456 (1973); J. Agr. Food. Chem. 21, 767 (1973)).

Various processes for the synthesis of these synthetic products are known.

The reaction of diazoacetic acid esters with 1,1-dichloro-4-methyl-1,3-pentadiene leads, after hydrolysis, to 2,2-dimethyl-3-(β,β-dichlorovinyl)-cyclopropanecarboxylic acid which is suitable for use as an intermediate for the synthesis of pyrethroids (Coll. Czech. Chem. Commun. 24, 2230 (1959)).

The ozonization of naturally occurring chrysanthemumic acid esters gives 2,2-dimethyl-3-formyl-cyclopropanecarboxylic acid esters as intermediates for the Wittig reaction with triphenyldichloromethylenephosphorane (South African Patent Specification No. 733,528).

However, these processes can be carried out on a relatively large scale only with difficulty.

Further processes which lead to 2,2-dimethyl-3-(β,β-dihalogenovinyl)-cyclopropanecarboxylic acids and esters have been disclosed. Thus, certain allyl alcohols are reacted with ortho-esters and subjected to a rearrangement reaction at 160° C. An addition reaction with CCl$_4$, which may take place by a free radical mechanism, and subsequent cyclization give the carboxylic acid derivatives, from which the acids mentioned above can be obtained. In this process, various by-products are formed in the individual reaction stages and some of these products can make it difficult to isolate intermediate stages and their presence is evidenced by reduced yield (German Offenlegungsschriften (German Published Specifications) Nos. 2,539,895 and 2,544,150).

The known processes for introducing, in particular, a halogenovinyl group in the 3-position of the cyclopropanecarboxylic acid have, according to circumstances, various disadvantages, of which the following can be particularly serious:

(1) formation of undesired by-products,
(2) relatively high reaction temperatures in some cases,
(3) several reaction stages and
(4) relatively low total yields over all reaction steps.

The processes mentioned above are thus ill-suited to the industrial preparation of many cyclopropane-carboxylic acid esters containing different substituents.

Furthermore, it has been found that vinyl-substituted cyclopropanecarboxylic acids can be obtained by allowing monochloroketene, produced in situ, to act on ethylenically unsaturated compounds (German Offenlegungsschrift (German Published Specification) No. 2,539,048).

However, this process is not universally applicable and can be carried out only with ethylenically unsaturated compounds wherein the double bond is activated by suitable substituents.

(1) The present invention provides a process for the preparation of a vinyl-substituted cyclopropanecarboxylic acid ester of the general formula

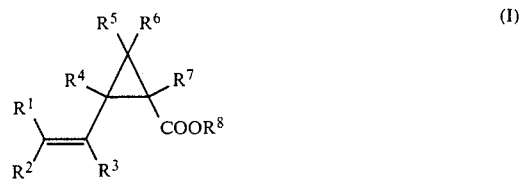

in which $R^1$, $R^2$ and $R^3$, which need not be identical, each represent hydrogen, halogen, CN, optionally substituted alkyl or alkenyl, aralkyl, aryl, alkoxycarbonyl, dialkylaminocarbonyl, acyloxy, alkylsulphonyl or arylsulphonyl, $R^4$, $R^5$, $R^6$ and $R^7$, which need not be identical, each represent hydrogen, optionally substituted alkyl or alkenyl, halogen, CN, aralkyl or aryl, it being possible for any of the pairs $R^1$ and $R^2$, $R^2$ and $R^3$, $R^1$ and $R^4$, $R^4$ and $R^5$, $R^4$ and $R^7$ and $R^5$ and $R^6$, conjointly with the adjacent carbon atom(s), to form a multimembered carbocyclic ring with up to 8 ring carbon atoms, and $R^8$ represents an alcoholic radical, in which process (1.1) an α-halogenocyclobutanone, of the general formula

in which $R^1$ to $R^7$ have the meanings stated above and

Hal represents halogen, is reacted with an alcoholate of the general formula

in which $R^8$ has the meaning stated above and

M represents an equivalent of an alkali metal cation or alkaline earth metal cation, if appropriate in the presence of a diluent, or (1.2) a cyclobutanone of the general formula

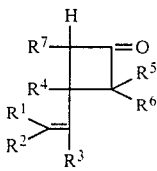
(IV)

in which
R¹ to R⁷ have the meanings stated above,
is halogenated, if appropriate in the presence of a diluent, and the halogenation product is subsequently reacted with an alcoholate of the general formula (III) above, or (1.3) an α-halogenocyclobutanone of the general formula

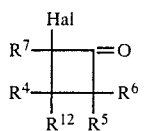
(V)

in which
$R^{12}$ represents a group

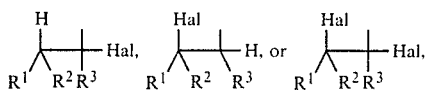

R¹ to R⁷ have the meanings stated above, and
Hal represents halogen,
is reacted with an alcoholate of the general formula (III) above, if appropriate in the presence of a diluent, or (1.4) a cyclobutanone of the general formula

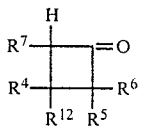
(VI)

in which
$R^{12}$ has the meaning stated above,
R¹ and R⁷ have the meanings stated above, and
Hal represents halogen,
is halogenated, if appropriate in the presence of a diluent, and the halogenation product is subsequently reacted with an alcoholate of the general formula (III), or in which (2), provided that a new vinyl-substituted cyclopropanecarboxylic acid ester of the general formula (I) is to be prepared
in which
R¹ and R², which may be identical or different, each have the meaning stated above,
R³ represents halogen, CN, $C_{2-6}$-alkyl or substituted $C_{1-6}$-alkyl and
R⁴ to R⁸ have the meanings stated above,
(2.1) a cyclopropanecarboxylic acid of the general formula

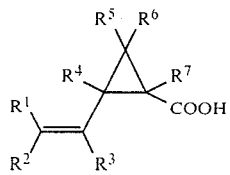
(VII)

in which
R¹ to R⁷ have the meanings stated under 2,
is reacted with an alcohol of the general formula

R⁸—OH       (VIII), in which
R⁸ has the meaning stated above,
if appropriate in the presence of a basic or acid catalyst and of a diluent and if necessary at an elevated temperature, or
(2.2) a cyclopropanecarboxylic acid of the formula (VII) is reacted with an inorganic or organic acid halide and the cyclopropanecarboxylic acid halide formed is subsequently reacted with an alcohol of the formula (VIII), if appropriate in the presence of a base, or
(2.3) the alkali metal, alkaline earth metal or ammonium salt of a cyclopropanecarboxylic acid of the formula (VII) is reacted with a compound of the general formula

R⁸—R⁹       (IX), in which
R⁸ has the meaning stated above and
R⁹ represents halogen, methanesulphonoxy, benzenesulphonoxy, p-toluenesulphonoxy or a radical —O—SO₂—O—R⁸, or
(2.4) a $C_1$–$C_4$ alkyl ester of a cyclopropanecarboxylic acid of the formula (VII) is reacted with an alcohol of the formula (VIII), if appropriate in a diluent and in the presence of a basic catalyst.

The process variants 1.1 to 1.4 for the preparation of the vinyl-substituted cyclopropanecarboxylic acid esters, some of which are known, are distinguished, in comparison with known processes for the preparation of such compounds, by the fact that, by choosing suitable starting compounds, it has been possible to make these vinyl-substituted cyclopropanecarboxylic acid esters easily, even on a large scale. In addition, the processes according to the invention are widely applicable and not limited to certain small groups of compounds. A further advantage of the process variants 1.1 to 1.4 is that it is possible to obtain the desired cyclopropanecarboxylic acid esters directly, without having to isolate the cyclopropanecarboxylic acids on which they are based. Process variant 1.2, in which cyclobutanones are used directly as the starting materials, without it being necessary to isolate the α-halogenocyclobutanones or cyclopropanecarboxylic acids which are possible as intermediate stages, is particularly advantageous.

(3) α-Halogenocyclobutanones of the formula (II) which can be used in process variant 1.1 are known (German Offenlegungsschrift (German Published Specification) No. 2,539,048) and can all be prepared in a simple manner:
(3.1) by halogenating a cyclobutanone of the general formula

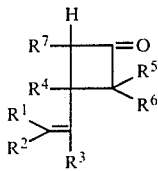 (IV)

in which
the radicals $R^1$ to $R^7$ have the meanings stated under 1, if appropriate is the presence of a diluent, or (3.2) by halogenating a cyclobutanone of the general formula

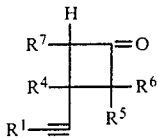 (X)

in which
the radicals $R^1$ and $R^4$ to $R^7$ have the meanings stated under 1,
if appropriate in the presence of a diluent, or (3.3) by halogenating a cyclobutanone of the general formula

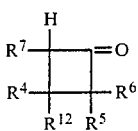 (VI)

in which
$R^{12}$ has the meaning stated under 1.3 and
$R^1$ and $R^7$ have the meanings stated under 1, if appropriate in the presence of a diluent.

(4) The new α-halogenocyclobutanones, which can be used in process variant 1.1, of the formula (II) in which
$R^1$ and $R^7$ have the meanings indicated under 1, provided that at least one of $R^1$, $R^2$ and $R^3$ has a meaning other than hydrogen, methyl or alkoxycarbonyl,
can be obtained, in addition to the processes indicated under 3.1 to 3.3, by reacting (4.1) a 1,3-diene of the general formula

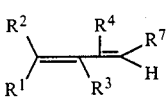 (XII)

in which
$R^1$ to $R^4$ and $R^7$ have the meanings indicated under 2,
with chloroketene of the formula

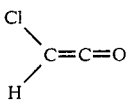 (XI)

which is optionally produced in situ, if appropriate in the presence of a diluent.

If a vinyl-substituted α-bromocyclobutanone is reacted with sodium ethylate in process variant 1.1, the course of the reaction can be represented by the following equation:

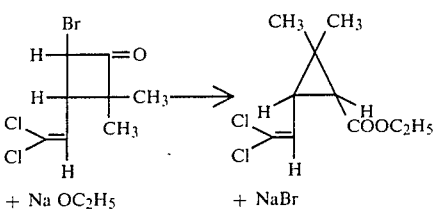

The α-halogenocyclobutanone of the formula (II) in which the radicals $R^1$ to $R^7$ have the meanings stated under 2, are preferably used in process variant 1.1.

Furthermore, particularly preferred α-halogenocyclobutanones of the formula (II) for use in process variant 1.1 are those in which $R^1$, $R^2$ and $R^3$, which need not be identical, each represent hydrogen, halogen (especially fluorine, chlorine or bromine), CN, straight-chain, branched or cyclic $C_{1-6}$-alkyl or alkenyl [either of which may be optionally substituted by halogen (especially fluorine or chlorine), $C_{1-4}$-alkoxy, CN or $C_{1-4}$-halogenoalkoxy], benzyl, phenylethyl, phenyl or naphthyl [any of which may be optionally substituted by halogen (especially chlorine), $C_{1-4}$-alkyl, $C_{1-4}$-halogenoalkyl, $NO_2$ or CN], $C_{1-4}$-alkoxycarbonyl, dialkylaminocarbonyl with 1–4 carbon atoms per alkyl moiety, $C_{1-4}$-alkylsulphonyl (especially methylsulphonyl), phenylsulphonyl [optionally substituted by halogen, $C_{1-4}$-alkyl, $C_{1-4}$-halogenoalkyl, $NO_2$ or CN] or $C_{1-4}$-acyloxy (especially acetoxy or trifluoroacetoxy), and $R^4$ to $R^7$, which need not be identical, each represent hydrogen, straight-chain, branched or cyclic $C_{1-6}$-alkyl or alkenyl [either of which may be optionally substituted by halogen, (especially fluorine or chlorine), $C_{1-4}$-alkoxy or CN], halogen (especially chlorine or bromine), CN or benzyl, phenylethyl, phenyl or naphthyl [any of which may be optionally substituted by halogen (especially chlorine), $C_{1-4}$-alkyl, $C_{1-4}$-halogenoalkyl, $NO_2$ or CN], it being possible for any of the pairs $R^1$ and $R^2$, $R^2$ and $R^3$, $R^1$ and $R^4$, $R^4$ and $R^5$, $R^4$ and $R^7$ and $R^5$ and $R^6$, together with the adjacent carbon atom(s), to form a 5 to 7 membered carbocyclic ring.

Especially preferred α-halogenocyclobutanones of the formula (II) are those in which $R^1$, $R^2$ and $R^3$, which need not be identical, each represent hydrogen, halogen (especially fluorine, chlorine or bromine), CN, acetoxy, benzenesulphonyl, methoxycarbonyl, phenyl, dimethylaminocarbonyl, chlorovinyl, methyl or ethyl, and $R^4$ to $R^7$, which need not be identical, each represent hydrogen, methyl, ethyl, cyclohexyl, chlorine or CN, it being possible for the pair $R^5$ and $R^6$ or the pair $R^4$ and $R^7$, together with the adjacent carbon atom(s), to form a 6-membered carbocyclic ring.

Particularly suitable α-halogenocyclobutanones of the formula ((II) are: 2,2-dimethyl-3-(α-methyl-β,β-dichlorovinyl)-cyclobutanone, 2,2-diethyl-3-(α,β-dichlorovinyl)-cyclobutanone, 2,2-dimethyl-3-(α,β,β-trifluorovinyl)-cyclobutanone, 2,2-diethyl-3-(α,β,β-trichlorovinyl)-cyclobutanone, 2,2-dimethyl-3-(α,β-dichlorovinyl)-cyclobutanone, 2,2-dimethyl-3-(β,β-dibromovinyl)-cyclobutanone, 2,2-dimethyl-3-(α-fluoro-β,β-dichlorovinyl)-cyclobutanone, 2,2-dimethyl-3-(β-chlorovinyl)-cyclobutanone, 2,2,3-trimethyl-3-(α,β,β-trifluorovinyl)-cyclobutanone, 2,2-dimethyl-3-(β,β-difluorovinyl)-cyclobutanone, 2-ethyl-2-methyl-3-

(β,β-dichlorovinyl)-cyclobutanone, 2-ethyl-2-methyl-3-(α,β,β-trichlorovinyl)-cyclobutanone, 2-ethyl-2,3-dimethyl-3-(α,β,β-trichlorovinyl)-cyclobutanone, 2,2-diethyl-3-(β,β-dibromovinyl)-cyclobutanone, 2-ethyl-2-methyl-3-(β,β-dibromovinyl)-cyclobutanone, 2-ethyl-2-methyl-3-(α-fluoro-β,β-dichlorovinyl)-cyclobutanone, 2,2-dimethyl-3-(α-ethyl-β,β-dichlorovinyl)-cyclobutanone, 2-ethyl-2,3-dimethyl-3-(β,β-dichlorovinyl)-cyclobutanone, 2,2-dimethyl-3-(α,β-dibromovinyl)-cyclobutanone, 2,2-dimethyl-3-(β-bromo-β-chlorovinyl)-cyclobutanone, 2,2-dimethyl-4-ethyl-3-(β,β-dichlorovinyl)-cyclobutanone, 2,2,4-trimethyl-3-(α,β-dibromovinyl)-cyclobutanone, 2,2-dimethyl-4-n-butyl-3-(β,β-dichlorovinyl)-cyclobutanone, 2-methyl-3-(α,β,β-trichlorovinyl)-cyclobutanone, 2,2-dimethyl-3-(β,β-dichlorovinyl)-cyclobutanone, 2,2-dimethyl-3-(α,β,β-trichlorovinyl)-cyclobutanone, 2,2,3-trimethyl-3-(α,β,β-trichlorovinyl)-cyclobutanone, 2,2-di-n-propyl-3-(α,β,β-trichlorovinyl)-cyclobutanone, 2,2-dimethyl-3-(α-cyano-β,β-dichlorovinyl)-cyclobutanone, 2,2-dimethyl-3-n-butyl-3-(β,β-dichlorovinyl)-cyclobutanone, 2,2-dimethyl-3-(β-chloro-β-methoxycarbonylvinyl)-cyclobutanone, 2,2-dimethyl-3-(β,β-dicyanovinyl)-cyclobutanone, 2,3-dimethyl-3-(β,β-dibromovinyl)-cyclobutanone, 2,2-dimethyl-3-(β,β-dibromovinyl)-4-n-butyl-cyclobutanone, 2,2-dimethyl-3-(α-chloro-β-acetoxyvinyl)-cyclobutanone, 2,2-di-n-butyl-3-methyl-3-(α-chloro-β-cyanovinyl)-cyclobutane, 2,2-dimethyl-3-(α-methylsulphonylvinyl)-cyclobutanone, 2,2-diethyl-3-(β,β-dichlorovinyl)-4-cyclohexyl-cyclobutanone, 2,3-dimethyl-2-chloro-3-(α,β,β-trichlorovinyl)-cyclobutanone, 2-methyl-2-phenyl-3-(β,β-dichlorovinyl)-cyclobutanone, 2,2-dimethyl-3-(β-chloro-β-phenylvinyl)-cyclobutanone, 2,2-dimethyl-3-(β,β-bis-(trifluoromethyl)-vinyl)-cyclobutanone and 2,2-dimethyl-3-(α,β,β-trichlorovinyl)-4-benzyl-cyclobutanone which are substituted in the 4-position by chlorine or bromine.

Spiro-cyclic cyclobutanones which are halogenated in the 3-position are: 3-(β,β-dichlorovinyl)-spiro[3,5]nonan-1-one, 3-(α,β,β-trichlorovinyl)-spiro[3,5]nonan-1-one, 3-(β,β-dibromovinyl)-spiro[3,5]nonan-1-one, 3-(β,β-dichlorovinyl)-spiro[3,4]octan-1-one, 3-(β,β-dichlorovinyl)-2-methyl-spiro[3,5]nonan-1-one, 3-(α,β-dichlorovinyl)-spiro[3,5]nonan-1-one and 3-(α,β,β-trifluorovinyl)-spiro[3,5]nonan-1-one.

Alcoholates of the formula (III) which are preferably employed in process variant 1.1 are: alkali metal and alkaline earth metal alcoholates, such as, for example, sodium methylate, sodium ethylate, lithium n-propylate and potassium tert.-butylate. However, alkali metal alcoholates of higher alcohols, such as benzyl alcohols substituted in the m-position by benzyl, furfuryl-3, furfuryl-2, m-fluorophenoxy, trichlorovinyloxy, phenoxy, β,β-dichlorovinyloxy, buta-1,3-dienyloxy or perchlorobuta-1,3-dienyloxy, or 4-phenyl-3,4-dichlorobut-2-enol, 4-phenyl-4-methyl-but-2-enol, 4-phenyl-3-chloro-4-methyl-but-2-enol, vitamin A alcohol, 5,-dichloropenta-2,4-dienol, pyrethrenolone and α-ethynyl-m-phenoxybenzyl alcohol, also find use.

Alcoholates of the formula (III) in which $R^8$ represents a radical of the general formula

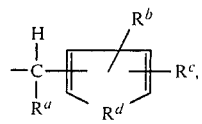

in which $R^a$ represents hydrogen, cyano or ethynyl, $R^b$ represents hydrogen, a $C_{1-4}$ alkyl radical, a phenoxy, benzyl or phenylthio group, or a vinyl or buta-1,3-dienyl radical which is optionally substituted by halogen, $R^c$ represents hydrogen, halogen or a $C_{1-4}$ alkyl radical and $R^d$ represents oxygen, sulphur or a vinylene group, are particularly suitable.

The process variant 1.1 according to the invention is preferably carried out in an inert organic solvent, such as methanol, if sodium methylate is used, or ethanol, if sodium ethylate is used, or an ether, such as diethyl ether, tetrahydrofuran or 1,2-dimethoxyethane, tetramethylenesulphone, dimethylformamide or a hydrocarbon, such as benzene or toluene. The reaction can be carried out at a temperature of about −30° to +150° C., preferably of about 20° to 60° C. Sometimes the components already react with one another sufficiently rapidly at 0° C. The reaction time depends on the reactants, the reaction temperature and the α-halogenoketone used, and can vary from about 1 to 10 hours.

Theoretically, one equivalent of an alcoholate is necessary for the ring contraction. However, the reaction can also be carried out with an excess of up to one equivalent of alcoholate or with an amount of alcoholate which is slightly less than the equivalent amount, namely about 0.1 equivalent less.

For working up, any excess of the alcoholate which may be present is neutralized with, for example, alcoholic hydrochloric acid, while cooling; the reaction mixture is then filtered and the cyclopropanecarboxylic acid ester is separated off by distillation or crystallization of the filtrate. However, an alternative procedure is to introduce the reaction mixture into hydrochloric acid, diluted with ice, and to extract the desired ester using an organic solvent.

(5) Cyclobutanones of the formula (IV) which can be used in process variant 1.2 are known (J.Org. Chem. 32, 2704 (1967); Houben-Weyl, Volume IV part 4, page 174 et seq.). They can be prepared in a simple manner by (5.1) reacting an α-chloroenamine of the general formula

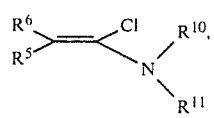

in which $R^5$ and $R^6$ have the meaning stated under 1 and $R^{10}$ and $R^{11}$, which may be identical or different, each represent $C_{1-4}$-alkyl or, with the adjacent N atom, form a heterocyclic ring which optionally also contains one or more further hetero-atoms, with an olefin of the general formula

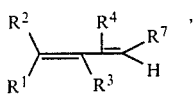

(XII)

in which
R[1] to R[4] and R[7] have the meanings stated under 1,
if appropriate in a diluent in the presence of a Lewis acid or a silver salt and subsequently hydrolyzing the product, if appropriate in the presence of an aqueous base or acid, or by (5.2) hydrolyzing an imonium salt of the general formula

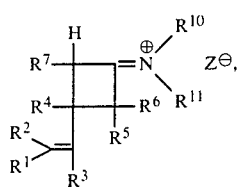

(XV)

in which
R[1] to R[7] have the meanings stated under 1,
R[10] and R[11] have the meanings stated under 5.1 and
Z represents an equivalent of an anion,
if appropriate in a diluent and if appropriate in the presence of an aqueous base or acid, or by (5.3) reacting a ketene of the general formula

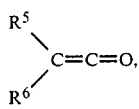

(XVI)

in which
R[5] and R[6] have the meanings stated under 1, with an olefin of the general formula (XII)
in which
R[1] to R[4] and R[7] have the meaning indicated under 1,
if appropriate in the presence of a diluent and if appropriate in the presence of a catalyst, or by (5.4) reacting a ketene of the general formula

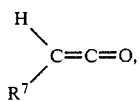

(XVII)

in which
R[7] has the meaning stated under 1,
with an olefin of the general formula

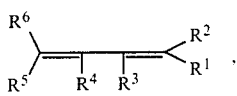

(XVIII)

in which
R[1] to R[6] have the meanings stated under 1,
if appropriate in the presence of a diluent and if appropriate in the presence of a catalyst, or by (5.5) reacting a ketene acylal of the general formula

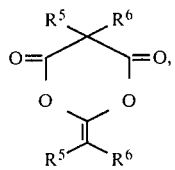

(XIX)

in which
R[5] and R[6] have the meanings stated under 1, with an olefin of the general formula (XII)
in which
R[1] to R[4] and R[7] have the meanings stated under 1,
if appropriate in a diluent and in the presence of a catalyst, or by (5.6) halogenating the vinyl group of a cyclobutanone of the general formula (IV)
in which
R[1] to R[7] have the meaning stated under 1, provided that one of R[1] to R[3] is hydrogen,
if appropriate in a diluent, and subsequently dehydrohalogenating the reaction product, or by (5.7) dehydrohalogenating a cyclobutanone of the general formula

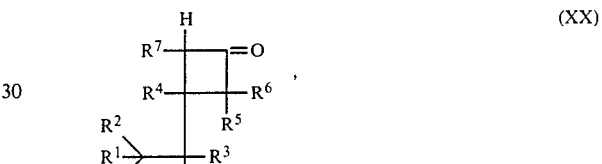

(XX)

in which
R[1] to R[7] have the meanings stated under 1, but at least one of the radicals R[1] to R[3] represents hydrogen,
if appropriate in a diluent, or by (5.8) hydrolyzing an imonium salt of the general formula

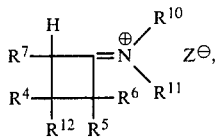

(XXI)

in which
R[1] to R[7] have the meanings stated under 1,
R[10], R[11] and Z have the meanings stated under 5.2 and
R[12] has the meaning stated under 1.3,
if appropriate in the presence of an aqueous base or acid and subsequently dehydrohalogenating the product, or by (5.9) reacting an α-chloroenamine of the general formula (XIII) in which
R[5], R[6], R[10] and R[11] have the meanings stated under 5.1,
with an olefin of the general formula

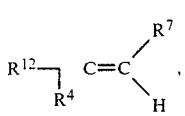

(XXII)

in which $R^{12}$, $R^4$ and $R^7$ have the meanings stated under 1 and 1.3, if appropriate in a diluent and in the presence of a Lewis acid or a silver salt, and subsequently hydrolyzing the product in the presence of an aqueous acid or base.

(6) Those cyclobutanones of the formula (IV) (which can be used in process variant 1.2) are new wherein $R^1$ to $R^7$ have the meanings stated under 1 and at least one of the radicals $R^1$, $R^2$ and $R^3$ to have a meaning other than hydrogen or methyl and $R^5$ has a meaning other than phenyl.

Preferred cyclobutanones of the formula (IV) for use in process variant 1.2 are those in which $R^1$, $R^2$ and $R^3$, which may be identical or different, each represent hydrogen, halogen (especially chlorine or bromine), CN, straight-chain, branched or cyclic $C_{1-6}$-alkyl or alkenyl [either of which may be optionally substituted by halogen (especially fluorine or chlorine), $C_{1-4}$-alkoxy, CN or $C_{1-4}$-halogenoalkoxy], benzyl, phenylethyl, phenyl or naphthyl [any of which may be optionally substituted by halogen (especially chlorine), $C_{1-4}$-alkyl, $C_{1-4}$-halogenoalkyl, $NO_2$ or CN], $C_{1-4}$-alkoxycarbonyl, dialkylaminocarbonyl with 1–4 carbon atoms per alkyl moiety, $C_{1-4}$-alkylsulphonyl (especially methylsulphonyl), phenylsulphonyl [optionally substituted by halogen, $C_{1-4}$-alkyl, $C_{1-4}$-halogenoalkyl, $NO_2$ or CN] or $C_{1-4}$-acyloxy, (especially acetoxy, or trifluoroacetoxy), and $R^4$ to $R^7$, which may be identical or different, each represent hydrogen, straight-chain, branched or cyclic $C_{1-6}$-alkyl or alkenyl [either of which is optionally substituted by halogen (especially fluorine or chlorine), $C_{1-4}$-alkoxy or CN], halogen (especially chlorine or bromine), CN or benzyl, phenylethyl, phenyl or naphthyl [any of which may be optionally substituted by halogen (especially chlorine), $C_{1-4}$-alkyl, $C_{1-4}$-halogenoalkyl, $NO_2$ or CN], it being possible for any of the pairs $R^1$ and $R^2$, $R^2$ and $R^3$, $R^1$ and $R^4$, $R^4$and $R^5$, $R^4$ and $R^7$ and $R^5$ and $R^6$, conjointly with the adjacent carbon atom(s), to form a 5 to 7-membered carbocyclic ring.

Cyclobutanones in which the radicals $R^1$ to $R^7$ have the meaning mentioned in process variant 1.1 as being especially preferred are particularly preferably employed in process variant 1.2.

Individual cyclobutanones which are advantageously employed are those from which the α-halogenocyclobutanones mentioned in process variant 1.1 are derived.

Halogenating agents which can be used in process variant 1.2 are: bromine, chlorine, mixtures of bromine and chlorine, sulphuryl chloride, N-halogenoimides, such as, for example, N-bromosuccinimide, and 2,4,4,5-tetrabromocyclohexa-2,5-dienone.

The following are preferably used: bromine, chlorine and mixtures of bromine and chlorine.

In the halogenation, the cyclobutanones and the halogenating agent are generally employed in equivalent amounts or with a slight excess of halogenating agent of about 0.1 to 0.2 equivalent.

The procedure is to bring together the cyclobutanone, diluent and halogenating agent and to allow the mixture to react. If appropriate, a catalyst, for example an acid, preferably HBr or acetic acid, is added to the mixture in order to catalyze the reaction. An alternative procedure is to add the halogenating agent to the initially introduced cyclobutanone and diluent at the rate at which it is consumed. If appropriate, the halogenation can also be carried out without the presence of a diluent.

Diluents which can be used in process variant 1.2 are inert organic solvents, such as hydrocarbons, for example hexane, benzene or toluene, chlorinated hydrocarbons, such as methylene chloride or carbon tetrachloride, ethers, such as diethyl ether, or esters, such as ethyl acetate.

The halogenation in process variant 1.2 is carried out, in general, at about 0° to 40° C., preferably at room temperature. The halogenation is carried out, in general, under normal pressure. The hydrogen halide which may be formed during the reaction can be removed, if appropriate, by bubbling nitrogen through the reaction solution.

After the halogenation has ended, an alcoholate of the formula (III) is added to the reaction solution without intermediate isolation of the reaction products. Alcoholates which can be used are preferably alkali metal or alkaline earth metal alcoholates, especially sodium or potassium alcoholates, of alcohols which have been indicated as being preferred in process variant 1.1.

The resulting reaction solution is added to a solution or suspension of the alcoholate in the corresponding alcohol or in an inert organic solvent, as has been described above. However, it is also possible to add a solution or suspension of the alcoholate to the resulting reaction solution. The procedure is generally carried out at a temperature of about −30° to 150° C., preferably about 20° to 60° C. The reaction time can vary from about 1 to 10 hours. The alcoholates are generally added to the reaction solution in an at least equimolar ratio, but appropriately in about a 1.5 to 1.7 molar ratio.

For working up, the alcoholate, which is optionally present in excess, is neutralized with, for example, alcoholic hydrochloric acid, while cooling; the reaction mixture is filtered and the resulting cyclopropanecarboxylic acid ester is separated off by distillation or crystallization of the filtrate. However, an alternative procedure can be to introduce the reaction mixture into hydrochloric acid, diluted with ice, and to extract the desired ester with an organic solvent.

The α-halogenocyclobutanones of the formula (V) which can be used in process variant 1.3 are new.

They are obtained by the process 3.3 described hereinbelow. However, they can also be obtained by halogenation or HCl addition to the corresponding vinyl-substituted α-halogenocyclobutanones by methods which are in themselves known.

α-Halogenocyclobutanones of the formula (V) in which $R^1$ to $R^7$ have the meanings mentioned above as being preferred or especially preferred in process variant 1.1 are preferably used in process variant 1.3.

Preferred alcoholates of the formula (III) which are used in process variant 1.3 are those which are indicated above as being preferred in process variant 1.1.

The procedure for the ring contraction of the halogenated cyclobutanone in process variant 1.3 is identical to that described in process variant 1.1. The alcoholates used are preferably those of $C_1$–$C_4$ alcohols since one equivalent of the alcoholate is consumed for the dehydrohalogenation and does not lead to the formation of the ester. This would be uneconomical in the case of expensive alcohols.

In addition to the ring contraction described, a dehydrohalogenation takes place in the side chain, and this requires a further equivalent of alcoholate.

The cyclobutanones of the formula (VI) which can be used in process variant 1.4 are new.

They can be prepared by processes 5.8 and 5.9 described herein below or are obtained by halogenating or adding HCl onto the corresponding vinyl-substituted cyclobutanones by processes which are in themselves known.

The cyclobutanones of the formula (VI), in which $R^1$ to $R^7$ have the preferred or especially preferred meanings indicated in process variant 1.1, are preferably used in process variant 1.4.

Alcoholates of the formula (III) which are preferably used are the same as those indicated in process variant 1.3.

The procedure in process variant 1.4 is identical to that described in process variant 1.2. As in process variant 1.3, a dehydrohalogenation of the side chain takes place simultaneously with the ring contraction in process variant 1.4 also.

The new vinyl-substituted cyclopropanecarboxylic acid esters of the formula (I) in which $R^1$ to $R^8$ have the meaning indicated under 2 can also be prepared by the process variants 2.1 to 2.4, which are also according to the invention.

The following may be mentioned as preferred new cyclopropanecarboxylic acid esters: the m-phenoxybenzyl ester of 2,2-dimethyl-3-($\alpha,\beta,\beta$-trichlorovinyl)-cyclopropanecarboxylic acid, 2-ethyl-2-methyl-3-($\alpha,\beta,\beta$-trichlorovinyl)-cyclopropanecarboxylic acid, 2,2-diethyl-3-($\alpha,\beta,\beta$-trichlorovinyl)-cyclopropanecarboxylic acid, 2,2-dimethyl-3-($\alpha,\beta,\beta$-trifluorovinyl)-cyclopropanecarboxylic acid, 2,2,3-trimethyl-3-($\alpha,\beta,\beta$-trichlorovinyl)-cyclopropanecarboxylic acid, 2,2-dimethyl-3-($\alpha$-fluoro-$\beta,\beta$-dichlorovinyl)-cyclopropanecarboxylic acid, 2,2-dimethyl-3-($\alpha$-cyano-$\beta,\beta$-dichlorovinyl)-cyclopropanecarboxylic acid, 2,2-dimethyl-3-($\beta,\delta,\delta$-trichlorobuta-1,3-dienyl)-cyclopropanecarboxylic acid, 1,2,2-trimethyl-3-($\alpha$-cyano-$\beta,\beta$-dichlorovinyl)-cyclopropanecarboxylic acid, 1,2,3-trimethyl-3-($\alpha,\beta,\beta$-trifluorovinyl)-cyclopropanecarboxylic acid, 2,2-dimethyl-3-($\alpha$-chloro-$\beta$-methylsulphonyl-vinyl)-cyclopropanecarboxylic acid, 2,2-diethyl-3-methyl-3-($\alpha$-cyano-$\beta,\beta$-dibromovinyl)- and 2-($\alpha$-fluoro-$\beta,\beta$-dichlorovinyl)-spiro[2,5]octane-1-carboxylic acid, the methyl esters of 2,2-dimethyl-3-($\alpha,\beta,\beta$-trichlorovinyl)-cyclopropanecarboxylic acid, 2,2-diethyl-3-($\alpha,\beta,\beta$-trichlorovinyl)-cyclopropanecarboxylic acid, 2,2,3-trimethyl-3-($\alpha,\beta,\beta$-trichlorovinyl)-cyclopropanecarboxylic acid, 2-methyl-3-($\alpha,\beta,\beta$-trichlorovinyl)-cyclopropanecarboxylic acid, 2-methyl-2-n-propyl-3-($\alpha$-fluoro-$\beta,\beta$-dibromovinyl)-cyclopropanecarboxylic acid, 1,2,2-trimethyl-3-($\alpha$-cyano-$\beta,\beta$-dichlorovinyl)-cyclopropanecarboxylic acid, 1,2,3-trimethyl-3-($\alpha,\beta,\beta$-trifluorovinyl)-cyclopropanecarboxylic acid and 2-ethyl-2-propyl-3-($\beta$-bromo-$\alpha,\beta$-dichlorovinyl)-cyclopropanecarboxylic acid, the ethyl esters of 2,2-dimethyl-3-($\alpha,\beta,\beta$-trichlorovinyl)-cyclopropanecarboxylic acid, 2,2-diethyl-3-($\alpha,\beta$-dichlorovinyl)-cyclopropanecarboxylic acid, 2,2-diethyl-3-($\alpha,\beta,\beta$-trichlorovinyl)-cyclopropanecarboxylic acid, 2,2-dimethyl-3-($\alpha,\beta,\beta$-trifluorovinyl)-cyclopropanecarboxylic acid, 2,2,3-trimethyl-3-($\alpha,\beta,\beta$-trichlorovinyl)-cyclopropanecarboxylic acid, 2,2-dimethyl-3-($\alpha$-chloro-$\beta$-acetoxyvinyl)-cyclopropanecarboxylic acid, 2,2-dimethyl-3-($\alpha$-fluoro-$\beta,\beta$-dichlorovinyl)-cyclopropanecarboxylic acid, 2,2-dimethyl-3-($\alpha$-cyano-$\beta,\beta$-dichlorovinyl)-cyclopropanecarboxylic acid, 1,2,2,3-tetramethyl-3-($\alpha,\beta,\beta$-trichlorovinyl)-cyclopropanecarboxylic acid, 2,2-dimethyl-3-($\beta,\delta,\delta$-trichlorobuta-1,3-dienyl)-cyclopropanecarboxylic acid, 2-($\alpha,\beta,\beta'$-trichlorovinyl)-spiro[2,5]octane-1-carboxylic acid, 2,2-dimethyl-3-($\alpha$-chloro-$\beta$-methylsulphonyl-vinyl)-cyclopropanecarboxylic acid and 2,2-dimethyl-3-[$\alpha$-chloro-$\beta,\beta$-bis-(trifluoromethyl)vinyl]-cyclopropanecarboxylic acid, the n-propyl esters of 2,2-diethyl-3-($\alpha,\beta,\beta$-trichlorovinyl)-cyclopropanecarboxylic acid, 2,2,3-trimethyl-3-($\alpha,\beta,\beta$-trichlorovinyl)-cyclopropanecarboxylic acid, 2-methyl-3-($\alpha,\beta,\beta$-trichlorovinyl)-cyclopropanecarboxylic acid, 1,2,3-trimethyl-3-($\alpha,\beta,\beta$-trifluorovinyl)-cyclopropanecarboxylic acid and 2-($\alpha,\beta,\beta$-trichlorovinyl)-spirohexane-1-carboxylic acid, the $\alpha$-cyano-m-phenoxybenzyl esters of 2,2-diethyl-3-($\alpha,\beta$-dichlorovinyl)-cyclopropanecarboxylic acid, 2,2-dimethyl-3-($\alpha,\beta,\beta$-trifluorovinyl)-cyclopropanecarboxylic acid, 2,2-dimethyl-3-($\alpha$-fluoro-$\beta,\beta$-dichlorovinyl)-cyclopropanecarboxylic acid, 2-methyl-2-n-propyl-3-($\alpha$-fluoro-$\beta,\beta$-dibromovinyl)-cyclopropanecarboxylic acid, 1,2,2,3-tetramethyl-3-($\alpha,\beta,\beta$-trichlorovinyl)-cyclopropanecarboxylic acid, 2-($\alpha,\beta,\beta$-trichlorovinyl)-spiro[2,5]octane-1-carboxylic acid, 1,2,3-trimethyl-3-($\alpha,\beta,\beta$-trifluorovinyl)-cyclopropanecarboxylic acid and 2,2-dimethyl-3-($\alpha$-chloro-$\beta,\beta$-bis-(trifluoromethyl)vinyl)-cyclopropanecarboxylic acid, the 5-benzyl-3-furylmethyl esters of 2,2-diethyl-3-($\alpha,\beta$-dichlorovinyl)-cyclopropanecarboxylic acid, 2,2-dimethyl-3-($\alpha,\beta,\beta$-trifluorovinyl)-cyclopropanecarboxylic acid, 2,2-dimethyl-3-($\alpha$-fluoro-$\beta,\beta$-dichlorovinyl)-cyclopropanecarboxylic acid, 1,2,2,3-tetramethyl-3-($\alpha,\beta,\beta$-trichlorovinyl)-cyclopropanecarboxylic acid and 2-($\alpha,\beta,\beta$-trichlorovinyl)-spiro[2,5]octane-1-carboxylic acid and the 3,4,5,6-tetrahydrophthalimidomethyl esters of 2,2-dimethyl-3-($\alpha,\beta,\beta$-trichlorovinyl)-cyclopropanecarboxylic acid, 2,2-dimethyl-3-($\alpha$-fluoro-$\beta,\beta$-dichlorovinyl)-cyclopropanecarboxylic acid and 2-($\alpha,\beta,\beta$-trichlorovinyl)-spiro[2,5]octane-1-carboxylic acid.

Cyclopropanecarboxylic acids of the formula (VII), or their salts, or their esters with $C_{1-3}$-alcohols of the formula (VIII), in which $R^1$, $R^2$ and $R^4$ to $R^7$ have the preferred or especially preferred meanings indicated in process variant 1.2 and $R^3$ represents chlorine, bromine, CN, straight-chain, branched or cyclic alkyl with 2-6 carbon atoms or straight-chain or cyclic alkyl which has up to 4 carbon atoms and is substituted by halogen, especially fluorine or chlorine, CN or $C_{1-4}$-alkoxy, are preferably employed in this process.

Individual cyclopropanecarboxylic acids, or their salts or their $C_{1-3}$-alkyl esters, which are advantageously employed are 2,2-dimethyl-3-($\alpha$-fluoro-$\beta,\beta$-dichlorovinyl)-cyclopropanecarboxylic acid, 2,2-dimethyl-3-($\alpha,\beta,\beta$-trichlorovinyl)-cyclopropanecarboxylic acid ethyl ester, 2,2-dimethyl-3-($\alpha,\beta$-dichlorovinyl)-cyclopropanecarboxylic acid, 2-trifluorovinyl-spiro[2,5]octane-1-carboxylic acid, sodium 2,2-diethyl-3-($\alpha,\beta,\beta$-trifluorovinyl)-cyclopropane carboxylate, 1,2,2-trimethyl-3-($\alpha,\beta,\beta$-trichlorovinyl)-cyclopropanecarboxylic acid methyl ester, lithium 2,2-dimethyl-3-($\alpha$-cyano-$\beta,\beta$-dichlorovinyl)-cyclopropane carboxylate, 2,2-dimethyl-3-($\alpha,\beta,\beta$-trifluorovinyl)-cyclopropanecarboxylic acid, sodium 2,2-dimethyl-3-($\alpha$-methylsulphonylvinyl)-cyclopropane carboxylate and 2-methyl-2,3-diethyl-3-($\alpha$-fluoro-$\beta,\beta$-dibromovinyl)-cyclopropanecarboxylic acid ethyl ester.

Process variant 2.1 can be carried out by employing a cyclopropanecarboxylic acid of the formula (VII) and an alcohol of the formula (VIII) in an at least equimolar ratio. In general, however, the reaction is carried out with an excess of alcohol.

Diluents which can be used are inert organic solvents.

Catalysts which can be used are acids, such as p-toluenesulphonic acid, benzenesulphonic acid, hydrochloric acid and sulphuric acid.

The reaction is in general, carried out at about 60° to 150° C.

Process variant 2.2 is carried out in general by reacting a cyclopropanecarboxylic acid of the formula (VII) with an equimolar amount of an acid halide to give the carboxylic acid halide and reacting this, without isolating it, with an alcohol of the formula (VIII) in the presence of a tertiary base.

If appropriate, the formation of the acid chloride is carried out in the presence of a diluent, such as benzene, toluene or methylene chloride, at a temperature of about 0° to 100° C.

Acid halides which may be used are thionyl chloride, phosphorus trichloride, phosphorus tribromide or benzoyl chloride.

According to process variant 2.3, the new cyclopropanecarboxylic acid esters of the general formula (I) are also obtainable by reacting a salt of the new cyclopropanecarboxylic acids with an alkylating agent, such as, for example, a halide or sulphonate, in an inert diluent.

Suitable salts are, for example, the alkali metal or ammonium salts; alkylating agents are, for example, benzyl chloride, benzyl bromide, m-phenoxybenzyl bromide or vitamin A bromide.

Suitable diluents are dimethylformamide, acetonitrile, pentan-3-one or acetone.

In general, the reaction is carried out at a reaction temperature of about 20° to 100° C., preferably about 25° to 80° C. The working up can be carried out by distillation after the salts which have precipitated during the reaction have been separated of; frequently water is added to the reaction mixture, the product is taken up in a solvent which is substantially water immiscible and the solvent is evaporated off. The esters thus obtained can be purified by distillation. If high-boiling esters, which can undergo decomposition during distillation, are obtained, they are freed from residues of solvent or alkylating agent in vacuo at temperatures of up to about 150° C.

According to process variant 2.3, the new cyclopropanecarboxylic acid esters of the general formula (I) in which $R^1$ to $R^8$ have the meanings indicated under 2 are also obtainable by reacting a salt of the new cyclopropanecarboxylic acids with an alkylating agent, such as, for example, a halide or sulphonate, in an inert diluent.

Suitable salts are, for example, the alkali metal or ammonium salts; alkylating agents are, for example, benzyl chloride, benzyl bromide or m-phenoxybenzyl bromide.

Suitable diluents are dimethylformamide, acetonitrile, pentan-3-one, or acetone.

In general, the reaction is carried out at a reaction temperature of about 20° to 100° C., preferably about 25° to 80° C. The working up can be carried out by distillation after the salts which have precipitated during the reaction have been separated off; frequently water is added to the reaction mixture, the product is taken up in a solvent which is substantially water immiscible and the solvent is evaporated off. The esters thus obtained can be purified by distillation. If high-boiling esters, which can undergo decomposition during distillation, are obtained, they are freed from residues of solvent or alkylating agent in vacuo at temperatures of up to 150° C.

According to process variant 2.4, the $C_{1-4}$-alkyl esters of the new cyclopropanecarboxylic acids according to formula (VII) can be transesterified in a manner which is in itself known. Thus, for example, it can be advantageous initially to prepare a $C_1-C_4$ alkyl ester, preferably the ethyl ester, of a new cyclopropanecarboxylic acid of the general formula (VII) by reacting an α-halogenocyclobutanone of the general formula (II) with a sodium alcoholate, for example sodium ethylate, and then to transesterify this lower alkyl ester with an alcohol which is of interest biologically, using a basic catalyst. Bases for this process are, for example, sodium alcoholates. Such transesterifications proceed between equimolar amounts of alcohol and ester, but, in general, the alcohol is used in excess and the lower alcohol formed during the reaction, such as, for example, ethanol, is removed by distillation. Solvents for the trans-esterification are, for example, toluene or xylene.

(7) Vinyl-substituted cyclopropanecarboxylic acids, which can be used in process variants 2.1 and 2.2, of the formula (VI) in which the radicals $R^1$ to $R^7$ have the meanings stated under 1 are known (German Offenlegungsschrift (German Published Specification) No. 2,539,048, DOS (German Published Specification) No. 2,544,150 and Nature 244, 456, (1973)).

They can be prepared by (7.1) reacting α-halogenocyclobutanones of the formula (II) in which $R^1$ to $R^7$ and Hal have the meanings stated under 1, with an aqueous base, if appropriate in a diluent, or by (7.2) halogenating cyclobutanones of the formula (IV) in which $R^1$ to $R^7$ have the meanings stated under 1, if appropriate in a diluent, and subsequently reacting the product with an aqueous base.

(8) The new cyclopropanecarboxylic acids of the formula (VII) in which $R^1$ to $R^7$ have the meanings stated under 2 are preferably obtained by this procedure.

Particularly preferably, the following new cyclopropanecarboxylic acids may be mentioned: 2,2-dimethyl-3-(α,β,β-trichlorovinyl)-cyclopropanecarboxylic acid, 2,2-diethyl-3-(α,β-dichlorovinyl)-cyclopropanecarboxylic acid, 2-ethyl-2-methyl-3-(α,β,β-trichlorovinyl)-cyclopropanecarboxylic acid, 2,2-diethyl-3-(α,β,β-trichlorovinyl)-cyclopropanecarboxylic acid, 2,2-dimethyl-3-(α,β,β-trifluorovinyl)-cyclopropanecarboxylic acid, 2,2,3-trimethyl-3-(α,β,β-trichlorovinyl)-cyclopropanecarboxylic acid, 2,2-dimethyl-3-(α-chloro-β-acetoxyvinyl)-cyclopropanecarboxylic acid, 2-methyl-3-(α,β,β-trichlorovinyl)-cyclopropanecarboxylic acid, 2,2-dimethyl-3-(α-fluoro-β,β-dichlorovinyl)-cyclopropanecarboxylic acid, 2-methyl-2-n-propyl-3-(α-fluoro-β,β-dibromovinyl)-cyclopropanecarboxylic acid, 2,2-dimethyl-3-(α-cyano-β,β-dichlorovinyl)-cyclopropanecarboxylic acid, 1-ethyl-2,2-dimethyl-3-(α,β-dichlorovinyl)-cyclopropanecarboxylic acid, 1,2,2,3-tetramethyl-3-(α,β,β-trichlorovinyl)-cyclopropanecarboxylic acid, 2,2-dimethyl-3-(β, δ,δ-trichlorobuta-1,3-dienyl)-cyclopropanecarboxylic acid, 2-(α,β,β-trichlorovinyl)-spiro[2,5]octane- 1-carboxylic acid, 2-($\alpha,\beta,\beta$-trifluorovinyl)-1-methyl-spiro[2,5]octane-1-carboxylic acid, 1,2,2-trimethyl-3-($\alpha$-cyano-$\beta,\beta$-dichlorovinyl)-cyclopropanecarboxylic acid, 2,2,3-trimethyl-3-($\alpha$-chloro-$\beta,\beta$-dicyanovinyl)-cyclopropanecarboxylic acid, 1,2,3-trimethyl-3-($\alpha,\beta,\beta$-trifluorovinyl)-cyclopropanecarboxylic acid, 2,2-dimethyl-3-($\alpha$-chloro-$\beta$-methoxycarbonyl)-cyclopropanecarboxylic acid, 2,2-dimethyl-3-($\alpha$-chloro-$\beta$-methylsulphonyl-vinyl)-cyclopropanecarboxylic acid, 2,2-diethyl-3-methyl-3-($\alpha$-cyano-$\beta,\beta$-dibromovinyl)-cyclopropanecarboxylic acid, 2-ethyl-2-propyl-3-($\beta$-bromo-$\alpha,\beta$-dichlorovinyl)-cyclopropanecarboxylic acid, 2,2-dimethyl-3-[$\alpha$-chloro-$\beta,\beta$-bis-(trifluoromethyl)-vinyl]-cyclopropanecarboxylic acid, 2-($\alpha$-fluoro-$\beta,\beta$-dichlorovinyl)-spiro[2,5]octane-1-carboxylic acid, 2-($\alpha,\beta,\beta$-trichlorovinyl)-spirohexane-1-carboxylic acid, 2,2-dimethyl-3-($\alpha$-chloro-$\beta$-dimethylaminocarbonyl-vinyl)-cyclopropanecarboxylic acid and 2-phenyl-3-($\alpha,\beta,\beta$-trichlorovinyl)-cyclopropane-carboxylic acid.

The new and known $\alpha$-halogenocyclobutanones which are used as starting materials in process variants 1.1, 1.3 and in process 7.1 are obtainable by processes 3.1 to 3.3 and 4.1.

Cyclobutanones of the formula (IV) in which $R^1$ to $R^7$ have the preferred and especially preferred meanings indicated under 1.1 are preferred and especially preferred in process 3.1.

Individual cyclobutanones which may be mentioned and which can be employed in process 3.1 are preferably those cyclobutanones from which the $\alpha$-halogenocyclobutanones indicated under 1.1 are derived.

Suitable halogenating agents for process 3.1 are those mentioned in process variant 1.2. However, bromine or chlorine is preferably used.

If appropriate, process 3.1 is carried out in a diluent. Suitable diluents are inert organic aprotic solvents, such as, for example, hydrocarbons and chlorinated hydrocarbons, such as methylene chloride, carbon tetrachloride, chloroform, 1,2-dichloroethane, n-hexane or ligroin; ethers, such as diethyl ether; and esters, such as ethyl acetate. In addition to the aprotic solvents, protic solvents can also be used, such as, for example, formic acid, acetic acid, propionic acid or butyric acid. Moreover, these can catalyze the formation of the $\alpha$-halogenocyclobutanone derivatives. Further suitable catalysts are, for example, hydrogen halide acids, such as hydrogen chloride, hydrogen bromide or hydrogen iodide; mineral acids, such as, for example, sulphuric acid, perchloric acid or phosphoric acid; and also Lewis acids, such as aluminum trichloride, ferric chloride, zinc chloride or titanium tetrachloride. If appropriate, the halogenation can also be catalyzed by UV light.

The reaction temperature for the halogenation can be chosen within a wide range. The reaction can take place, both at $-70°$ C. and at $+80°$ C., depending on the structure of the cyclobutanone derivative to be halogenated. A temperature range of about $-10°$ to $+40°$ C., preferably about 15° to 25° C., proves useful for the preparation. Specifically, the halogenation can be carried out by introducing the halogen into the reaction solution incrementally, the rate of the addition depending on the conversion of the halogen, that is to say the addition of a further amount of halogen is made only when halogen which has previously been introduced has reacted. Another method used at times is to add together the reactants (cyclobutanone derivative and halogen and, if appropriate, solvent and catalyst) and to allow them to react at 15° to 25° C. A further variant is to drive out part of the hydrogen halide, formed during the reaction, from the reaction solution with nitrogen or to remove it by reaction with a basic compound, such as, for example, calcium carbonate or sodium carbonate.

The working up of the reaction solution can be so carried out that the hydrogen halide is driven out with nitrogen or air and the reaction solution is employed direct, if necessary after removing excess halogen with sodium thiosulphate, in process variant 1.1 or process 7.1, especially if, by reaction with an aqueous alkali metal base, the corresponding cyclopropanecarboxylic acid is to be obtained or if, by reaction with an alkali metal salt of a $C_1$–$C_4$ alcohol, such as ethanol, a cyclopropanecarboxylic acid ester of this $C_1$–$C_4$ alcohol is to be obtained. The crude $\alpha$-halogenoketone can be obtained free from hydrogen halide by washing with water, if appropriate with the addition of a solvent which is immiscible with water, and can be isolated in the pure form by crystallization or distillation.

The cyclobutanones of the general formula (X) which can be used in process 3.2 are new.

They can be obtained by reacting known cyclobutenones (Houben-Weyl, Volume IV part 4, page 174 et seq.) with organo-metallic compounds, such as ethynylmagnesium bromide or propargyllithium, with the addition of catalysts, such as copper salts, which promote a 1,4-addition.

The resulting 3-ethynylcyclobutanones are halogenated both in the $\alpha$-position relative to the keto group and on the triple bond. It is also possible to add hydrogen halide onto the triple bond before the halogenation and thus to obtain 1-halogenovinyl- or 2-halogenovinyl-substituted cyclobutanones instead of 1,2-dihalogenovinyl-substituted cyclobutanones.

The procedure of process 3.2 corresponds to that described in process 3.1, with the proviso that, where appropriate, 2 equivalents of halogenating agent are necessary for the halogenation.

The cyclobutanones of the general formula (VI) which can be used in process 3.3 are new; they can be obtained by the process described under 5.9.

The procedure of process 3.3 also corresponds to that described in process 3.1.

Some of the new $\alpha$-halogenocyclobutanones of the formula (II) in which $R^1$ to $R^7$ have the meaning indicated under 4 can also be obtained, according to the invention, by process 4.1.

The 1,3-dienes employed in process 4.1 are known or can be obtained by known methods. 1,3-Dienes of the formula (XII) in which $R^1$ to $R^7$ have the preferred meanings indicated under 1.1 are preferably employed.

1,3-Dienes of the formula (XII) in which $R^1$ to $R^7$ have the especially preferred meaning indicated under 1.1 are particularly preferred.

Particularly suitable 1,3-dienes of the formula (XII) are those indicated in process 5.1.

Chloroketene, which can be used in process 4.1, is known; if appropriate, it can be prepared in situ. With regard to the process conditions for this reaction, the conditions described in German Offenlegungsschrift (German Published Specification) No. 2,539,048 may be referred to.

As already mentioned, some of the cyclobutanones which can be used in process variant 1.2 and processes 3.1 to 3.3 and 7.2 are new. Their preparation is carried out by processes 5.1 to 5.9. Starting materials of the formulae (IV) (XII), (XIII), (XV), (XVI), (XVII), (XVIII), (XIX), (XX), (XXI), and (XXII) in which $R^1$-$R^7$ have the preferred and particularly preferred meaning indicated under 1.1 are preferably and particularly preferably employed in these processes. $R^{10}$ and $R^{11}$ preferably represent methyl or ethyl or, conjointly with the adjacent N atom, form a piperidine or morpholine ring.

The addition of a ketene or masked ketene (acylal or α-chloro-enamine) onto a double bond is common to processes 5.1 to 5.5 and 5.9. Cycloaddition reactions with ketenes to give 4-membered cyclic ketones proceed strictly stereospecifically, but frequently regiounspecifically. The more rich in electrons the double bond of the olefin, the more readily they occur. Thus, for example, dimethylketene adds onto 1-dialkylaminoalkenes or 1-alkoxyalkenes considerably better than onto the corresponding unsubstituted alkene. The cycloaddition of α-chloro-enamines on to 1,3-dienes having electron-attracting substituents, which proceeds unexpectedly smoothly, proves particularly valuable for the preparation. The cyclobutanones of the general formula (IV) are obtained in high yields under mild reaction conditions after the hydrolysis of the imonium salts which are formed as intermediates. A particular characteristic of this reaction is the observed regiospecificity of the addition. Indications of the formation of the regio-isomeric cyclobutanones are not obtained.

Specific examples of the α-chloro-enamines of the general formula (XIII) which are employed in process 5.1 are: 1-chloro-1-dimethylamino-2-methyl-1-propene, 1-chloro-1-piperidino-2-methyl-1-propene, 1-chloro-1-diethylamino-2-methyl-1-propene, 1-chloro-1-dimethylamino-1-propene, 1-chloro-1-morpholino-2-methyl-1-propene, 1-chloro-1-methylethylamino-2-methyl-1-propene, 1-chloro-1-dimethylamino-2-ethyl-1-butene, 1-chloro-1-dimethylamino-2-methyl-1-butene, (1-chloro-1-dimethylamino-methylene)-cyclohexane, 1,2-dichloro-1-dimethylamino-2-methyl-1-propene and 1-chloro-1-dimethylamino-2-methyl-2-phenyl-1-propene.

These α-chloro-enamines are known or can be prepared by known processes.

A large number of olefins of the general formula (XII) can be used as reactants in the cycloaddition reaction according to process 5.1, for example: 1-chlorobuta-1,3-diene, 2-chlorobuta-1,3-diene, 1,1-difluorobuta-1,3-diene, 1,1,2-trifluorobuta-1,3-diene, 1,1,2-trichlorobuta-1,3-diene, 1,1-dichlorobuta-1,3-diene, 1,1-dichloro-2-fluorobuta-1,3-diene, 1,1-dichloro-2-methylbuta-1,3-diene, 1,1-dichloro-2-ethylbuta-1,3-diene, 1,1-dichloro-3-methylbuta-1,3-diene, 1,1,2-trifluoro-3-methylbuta-1,3-diene, 1,1,2-trichloro-3-methylbuta-1,3-diene, 1,1-dicyanobuta-1,3-diene, 1,1-dicyano-2-methylbuta-1,3-diene, 1,1-difluoro-2-chlorobuta-1,3-diene, 1,1,2-trichloro-3-cyanobuta-1,3-diene, 1,1-dichloro-2-bromobuta-1,3-diene, 2-chloro-3-methylbuta-1,3-diene, 1,2-dichlorobuta-1,3-diene, 1,2-dibromobuta-1,3-diene, 1,1-dibromobuta-1,3-diene, 1,1-dibromo-2-fluorobuta-1,3-diene, 1,1-dibromo-2-chlorobuta-1,3-diene, 1,1-dichloropenta-1,3-diene, 1,1-dichloro-hexa-1,3-diene, 1,1,2-trichloro-penta-1,3-diene, 1,1-dichloro-3-methylpenta-1,3-diene, 1,1,2-trichloro-3-methylpenta-1,3-diene, 1,1-dichloro-hepta-1,3-diene, 1,1,2-trichloro-hepta-1,3-diene, 1,1-dichloro-octa-1,3-diene, 1,1-dichloro-nona'-1,3-diene, 1,1-dibromo-penta-1,3-diene, 1-acetoxy-2-chloro-buta-1,3-diene, 1,1-bis-trifluoromethyl-buta-1,3-diene, 2-methanesulphonyl-buta-1,3-diene, 1,1-dibromo-2-fluoro-penta-1,3-diene, 1,1-dichloro-2-fluoro-penta-1,3-diene, 1,3-dibromo-2-methyl-penta-1,3-diene, 1-(β,β-dichlorovinyl)-1-cyclohexene, 1-vinyl-2-chloro-1-cyclohexene and 1-(β,β-dichlorovinyl)-1-cyclopentene.

For process 5.1, it is necessary to convert the α-chloroenamine into a reactive form. This can be carried out by reacting the α-chloro-enamine with, for example, silver tetrafluoroborate. Other salts, such as, for example, silver hexafluorophosphate, silver perchlorate or silver hexafluoroarsenate can be used. With regard to isolating the cyclobutanones of the general formula (IV), it is cheaper to use zinc chloride for carrying out the cycloaddition reaction with α-chloro-enamines according to process 5.1. Thus, in the case of addition on to halogenovinyl-substituted olefins under the mild reaction conditions used (see below), no reaction of the zinc chloride with the diene takes place. However, a large number of other compounds, such as, for example, Lewis acids (iron III) chloride, titanium tetrachloride, aluminum chloride, boron trifluoride or tin chloride) can be used in process 5.1.

The reaction of an α-chloro-enamine of the general formula (XIII) with an olefin of the general formula (XII) can be carried out by initially introducing the olefin, if appropriate in a solvent, together with a Lewis acid and adding the α-chloro-enamine dropwise, if appropriate in a solvent, while stirring. An exothermic effect can occur in this procedure. However, an alternative procedure can be initially to introduce the α-chloro-enamine, if appropriate in a solvent, to produce the reactive keteneimonium cation by adding a Lewis acid and to add the olefin dropwise, if appropriate in a solvent. An exothermic effect can also occur in this procedure. A further variant is to add together the reactants (α-chloro-enamine, Lewis acid and olefin), if appropriate in a solvent, and to stir the mixture. An exothermic effect can again occur here. Solvents which can be employed are halogenated hydrocarbons, such as, for example, methylene chloride, chloroform, carbon tetrachloride, 1,2-dichloroethane, 1,1,2,2-tetrachloroethane or 1,2-dichloroethylene, or acetonitrile, ethers or acetic acid esters, and also, for example, hydrocarbons, such as cyclohexane or petroleum ether, and also tetramethylene-sulphone or dimethylformamide.

The cycloaddition of an α-chloro-enamine onto an olefin in the presence of a Lewis acid is a reaction which proceeds stoichiometrically. However, it is advisable to employ a small excess of α-chloro-enamine and Lewis acid (maximum about 20%).

The reaction temperature can be chosen within a wide range. Thus, the reaction according to the invention can be carried out both at about −10° C. and +80° C. In many cases it has been shown that the cycloaddition reaction already occurs in the temperature range of 20° to 40° C., which is easy to control industrially, that is to say at room temperature or slightly above. A reaction time of about ½ to 24 hours is sufficient for a complete conversion.

For working up, the reaction mixture of process 5.1 is hydrolyzed by adding water, an aqueous base or an acid. In this procedure, the cyclobutanone-imonium salt, which is formed as an intermediate, is converted into the cyclobutanone derivative of the general formula (IV), if appropriate by warming the solution to a temperature of about 20° to 100° C., preferably about 40° to 60° C., and this cyclobutanone derivative is separated off by extraction with an organic solvent, such as, for example, toluene or dibutyl ether. By means of fractional distillation, if appropriate under reduced pressure, and/or crystallization it can be obtained in an analytically pure form for characterization. In many cases the purification is superfluous and the crude cyclobutanone can be employed directly in process variant 1.2 or processes 7.2 or 3.1. A prerequisite for this is that the solvent used for the extraction or cycloaddition reaction does not react with the halogenating agent.

The imonium salts which can be used in processes 5.2 or 5.8 are new; they are prepared by process 9.1 or 9.2 (see below).

Ketenes which can be used in processes 5.3 and 5.4 are known or can be prepared in a manner which is in itself known by (a) dehalogenating an α-halogenocarboxylic acid halide, for example α-bromoisobutyric acid bromide, in an inert solvent, such as, for example, ether or ethyl acetate, with zinc, if appropriate activated zinc, in an inert gas atmosphere (nitrogen) and distilling off the ketone formed, together with the inert solvent, the solvent and ketene being employed directly for the cycloaddition reaction (Houben-Weyl, Volume IV, part 4, page 174 et seq.); or (b) dehydrohalogenating acid chlorides, for example isobutyric acid bromide, with a tertiary amine, such as, for example, triethylamine or dicyclohexyl-ethylamine; or (c) reacting an α-diazoketone with mercury oxide; or (d) dissociating a ketene dimer, for example 2,2,4,4-tetramethylcyclobutane-1,3-dione, by the action of heat.

Ketene acetals which can be used in process 5.5 are known from German Auslegeschrift (German Published Specification) No. 1,199,259 and can be prepared by the processes described there.

The cyclobutanones which can be used in process 5.6 are new; they can be prepared by processes 5.1 to 5.5 and 5.8.

The cyclobutanones which can be used in process 5.7 are new; they can be prepared by adding halogen onto the vinyl group of cyclobutanones which can be prepared according to processes 5.1 to 5.5 and 5.8.

Process 5.9 can be carried out under the same conditions as indicated for process 5.1. The cyclobutanone-imonium salts formed as intermediates in these processes are hydrolyzed, without isolating them, to the corresponding cyclobutanones (see above).

The conversion, to be carried out in processes 5.2 and 5.8, of an isolated cyclobutanone-imonium salt of the general formulae (XV) and (XXI) into the corresponding cyclobutanone is carried out analogously to the procedure described in process 5.1. The conversion can also be carried out by subjecting the reaction solution, which has optionally been acidified or rendered alkaline, to steam distillation and separating off the cyclobutanone derivative from the steam distillate by extraction with an organic solvent and then, as given above, purifying. The zinc salts which remain in the aqueous phase, for example if dry zinc chloride is used as the Lewis acid, can be recovered by working up.

Processes 5.3 to 5.5 are carried out in an autoclave or bomb tube under pressure, for example analogously to the reaction conditions indicated in German Offenlegungsschrift (German Published Specification) No. 1,199,259.

(9) The imonium salts of the general formulae (XV) and (XXI) which can be used in processes 5.2 and 5.8 are new. They are obtained when (9.1) an α-chloroenamine of the general formula (XIII) in which $R^5$, $R^6$, $R^{10}$ and $R^{11}$ *have the meanings stated under* 5.1, is reacted with an olefin of the formula (XIV) in which $R^1$ to $R^4$ and $R^7$ have the meanings stated under 5.1, if appropriate in a diluent and in the presence of a silver salt, or when (9.2) an α-chloroenamine of the general formula (XIII), in which $R^5$, $R^6$, $R^{10}$ and $R^{11}$ have the meanings stated under 5.1, is reacted with an olefin of the formula (XXII) in which $R^1$ to $R^4$ and $R^7$ have the meanings stated under 5.9, if appropriate in a diluent and in the presence of a silver salt.

The reaction in processes 9.1 and 9.2 is carried out as described for process 5.1. It is generally carried out in the presence of a stoichiometric amount of a silver salt, such as silver perchlorate, silver hexafluorophosphate, silver hexafluoroarsenate or, preferably, silver tetrafluoroborate. After the addition reaction of the α-chloroenamine and the olefin has been carried out, which is effected by a procedure analogous to that described in 5.1, the silver chloride formed is filtered off, the solvent is distilled off from the filtrate and the residue is crystallized.

The vinyl-substituted cyclopropanecarboxylic acids, or their salts, which can be used for process variants 2.1 to 2.3 can be obtained by processes 7.1 or 7.2.

In process 7.1, the α-halogenoketone is reacted with water in the presence of a base; the salt, which is formed, of the cyclopropanecarboxylic acid is separated off and the acid is liberated by acidifying the alkaline solution with a mineral acid. This conversion can be carried out, if appropriate, with the addition of a solvent, such as, for example, toluene, methylene chloride, lower alcohols, such as ethanol or isopropanol, or dibutyl ether.

The reaction temperature can be chosen relatively freely; it can be about 0° to 100° C., preferably about 20° to 40° C. Alkali metal or alkaline earth metal hydroxides, such as sodium hydroxide, potassium hydroxide, lithium hydroxide or barium hydroxide; or tertiary amines, such as triethylamine or triethanolamine, can be used as bases; sodium hydroxide or potassium hydroxide is preferably employed.

At least two equivalents of a monoacidic base are necessary for complete conversion of the α-halogenocyclobutanone into the salt of the cyclopropane carboxylic acid. Consequently, the α-halogenoketone of the general formula (II) is also reacted with about 2 to 8 equivalents, preferably about 2 to 4 equivalents, of a monoacidic base.

The liberation of the acid from its salt can be effected by adding aqueous mineral acid, such as, for example, hydrochloric acid, sulphuric acid or phosphoric acid. The resulting cyclopropanecarboxylic acid can be purified by distillation or crystallization. In many cases, the acids are obtained in such a pure form that they can be further processed directly.

In the procedure of process 7.2, a cyclobutanone of the general formula (IV) is initially halogenated. In this procedure, the reaction is carried out as indicated in process 3.1.

As already mentioned, the cyclopropanecarboxylic acid esters obtainable by the processes according to the invention are suitable for combating animal pests and as intermediates for the preparation of active compounds for combating animal pests.

The active compounds are well tolerated by plants, have a favorable level of toxicity to warm-blooded animals, and can be used for combating arthropod pests, especially insects and acarids which are encountered in agriculture, in forestry, in the protection of stored products and of materials, and in the hygiene field. They are active against normally sensitive and resistant species and against all or some stages of development. The above-mentioned pests include: from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.; from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp. and Linognathus spp.; from the order of the Mallophaga, for example Trichodectes spp. and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes seneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.; from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *hortulanus Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.; from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with protection agents, such as other insecticides, or acaricides, nematicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, which comprises applying to at least one of correspondingly (a) such insects, and (b) the corresponding habitat thereof, i.e. the locus to be protected, e.g. to a growing crop, to an area where a crop is to be grown or to a domestic animal, a correspondingly combative or toxic amount, i.e. an insecticidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, pouring, fumigating, and the like.

It will be realized, of course, that the concentration of the particular active compound utilized in the admixture with the carrier vehicle will depend upon the intended application. Therefore, in special cases it is possible to go above or below the aforementioned concentration ranges.

The following preparative examples illustrate the processes according to the invention. Where spectroscopic data are indicated, they relate, in the case of IR spectra, to characteristic absorption maxima; in the case of NMR spectra they also relate to tetramethylsilane as an internal standard.

The symbols used denote: s=singlet, d=doublet, t=triplet, q=quartet, m=multiplet, br=broad and do=double.

EXAMPLE 1

Preparation of 2,2-dimethyl-3-($\alpha,\beta,\beta$-trichlorovinyl)-cyclobutanone A solution of 10.0 g of 2,2-dimethyl-3-($\alpha,\beta,\beta$-trichlorovinyl)-cyclobutanone-dimethylimonium tetrafluoroborate in 200 ml of water was warmed to 40°–60° C. for 30 minutes. An oil separated out which was extracted with methylene chloride. Drying the methylene chloride phase with sodium sulphate and concentration gave 6.1 g (90%) of 2,2-dimethyl-3-($\alpha,\beta,\beta$-trichlorovinyl)-cyclobutanone.

EXAMPLE 2

Preparation of 2,2-dimethyl-3-($\beta,\beta$-dichlorovinyl)-cyclobutanone 74.0 g (0.54 mol) of anhydrous zinc chloride were added to 56.0 g (0.45 mol) of 1,1-dichlorobuta-1,3-diene in 400 ml of methylene chloride, while stirring, and 60.0 g (0.45 mol) of 1-chloro-1-dimethylamino-2-methyl-1-propene in 300 ml of methylene chloride were then added dropwise, while stirring. During this procedure, the temperature of the reaction solution rose from 18° C. initially to 35°–40° C. After stirring for 2 hours under reflux, the mixture was cooled to 20° C. and, after standing overnight (15 hours) at 15° to 20° C., 1,200 ml of 1N NaOH were added dropwise, while stirring. 300 ml of methylene chloride were added, the mixture was acidified with 10% strength aqueous hydrochloric acid and the phases were separated. The organic phase was washed with water until it gave a neutral reaction, clarified over anhydrous sodium sulphate and evaporated. This gave 85.1 g of a yellow-brown oil, which was subjected to fractional distillation.

Yield: 73.5 g (84.5%) of a colorless oil of boiling point 100°–104° C./12 mm Hg; $n_D^{20} = 1.4912$.

IR (CCl$_4$) 1,790 cm$^{-1}$ (CO).

NMR (CDCl$_3$) δ 1.13 s (3H), 1.29 s (3H), 2.80–3.30 m (3H) and 5.90–6.10 ppmm (1H).

C$_8$H$_{10}$Cl$_2$O: (193.1); calculated C 49.76, H 5.22, Cl 36.73; found 49.8, 5.33, 36.1.

EXAMPLE 3

Preparation of 4-bromo-2,2-dimethyl-3-(β,β-dichlorovinyl)-cyclobutanone

A solution of 1.6 g (0.01 mol) of bromine in 4.5 ml of glacial acetic acid was added dropwise at 20° C. to a solution of 1.95 g (0.01 mol) of 2,2-dimethyl-3-(β,β-dichlorovinyl)-cyclobutanone in 2 ml of glacial acetic acid at such a rate that the reaction solution was decolorized before each addition of bromine. After subsequently stirring for 3 hours at 20° C., the reaction mixture was added to ice. The oil which had separated out was taken up in methylene chloride, the methylene chloride solution was washed with water until it gave a neutral reaction and clarified over anhydrous sodium sulphate and the organic phase was concentrated. This gave 2.72 g of a yellow-colored oil which, according to the NMR spectrum, no longer contained the starting ketone. Instead of this, signals occurred which indicated the presence of the two stereoisomeric 4-bromo-2,2-dimethyl-3-(β,β-dichlorovinyl)-cyclobutanones.

EXAMPLE 4

Preparation of 2,2-dimethyl-3-(α,β,β-trichlorovinyl)-cyclobutanone-dimethyliminium tetrafluoroborate 7.0 g (0.052 mol) of 1-chloro-1-dimethylamino-2-methyl-1-propane in 15 ml of methylene chloride were added dropwise to a suspension of 10.2 g (0.052 mol) of silver tetrafluoroboratain 70 ml of methylene chloride and 11.0 g (0.07 mol) of 1,1,2-trichlorobutadiene in the course of one hour at −60° C., while stirring. The reaction mixture was allowed to warm to 20°–25° C. and after being left to stand (15 hours) silver chloride was filtered off. Evaporation of the filtrate in vacuo left 21.07 g of a cycloadduct which, when recrystallized twice from chloroform/ether, gave 10.3 g of colorless crystals of melting point 129°–131° C.

C$_{10}$H$_{15}$BCl$_3$F$_4$N: (342,4); Calculated C 35.08, H 4.42, N 4.09; Found 35.1, 4.31, 4.14.

NMR (CD$_3$CN): δ 1.40 s (3H), 1.63 s (3H), 3.45 m (6H) and 3.5–4.0 ppm m (3H).

EXAMPLE 5

Preparation of 2,2-dimethyl-3-(β,β-dichlorovinyl)-cyclopropanecarboxylic acid

A mixture of the isomeric 4-bromo-2,2-dimethyl-3-(β,β-dichlorovinyl)-cyclobutanones, obtained from 0.01 mol of 2,2-dimethyl-3-(β,β-dichlorovinyl)-cyclobutanone according to Example 3, was stirred with 15 ml of 2N NaOH overnight (15 hours) at 20° C. The neutral products were extracted with ether, the alkaline aqueous phase was acidified with 10% strength aqueous hydrochloric acid and the acids were extracted with ether. Washing the ether extract with saturated sodium chloride solution and subsequent clarification over sodium sulphate (anhydrous) gave, after evaporating the organic phase, 1.35 g (65%) (relative to 2,2-dimethyl-3-(β,β-dichlorovinyl)-cyclobutanone employed) of crystalline 2,2-dimethyl-3-(β,β-dichlorovinyl)-cyclopropanecarboxylic acid which, according to the NMR spectrum, was a 22:78 mixture of the cis-trans isomers. Fractional crystallization from n-hexane gave sterically homogeneous 2,2-dimethyl-3-trans-(β,β-dichlorovinyl)-cyclopropanecarboxylic acid of melting point 87° to 89° C.

IR (CCl$_4$) 1,705 cm$^{-1}$ (CO).

NMR (CDCl$_3$) δ 1.20 s (3H), 1.32 s (3H), 1.55 d (1H, J=5.5 Hz) 2.25 dod (1H, J=8 Hz and 5.5 Hz), and 5.63 ppm d (1H, J=8 Hz).

After separating off the dominant trans-acid from a relatively large amount of crude acid, the sterically homogeneous 2,2-dimethyl-3-cis-(β,β-dichlorovinyl)-cyclopropanecarboxylic acid was obtained by fractional crystallization from pentane.

Melting point 92° to 94° C.

EXAMPLE 6

Preparation of 2,2-dimethyl-3-(β,β-dichlorovinyl)-cyclopropanecarboxylic acid ethyl ester A solution of 1.6 g (0.01 mol) of bromine in 5 ml of carbon tetrachloride was added dropwise, to the point of decolorization, to 1.95 g (0.01 mol) of 2,2-dimethyl-3-(β,β-dichlorovinyl)-cyclobutanone in 5 ml of carbon tetrachloride, which contained 5% of hydrogen bromide at 25° C. The mixture was subsequently stirred for 2 hours, the hydrogen bromide formed was removed by passing a dry stream of nitrogen through and the reaction solution was concentrated. The residue was taken up in 15 ml of absolute ether and the ether solution was added dropwise to a suspension of 0.9 g of sodium ethylate in 10 ml of absolute ether, while cooling with ice. The mixture was subsequently stirred for 2 hours and the temperature of the reaction mixture was allowed to rise to 20° to 25° C. The solution, which had an alkaline reaction, was neutralized with ethanolic hydrochloric acid and then added to ice. Extraction with ether, clarification of the ether phase over anhydrous sodium sulphate and concentration gave, after fractional distillation, 1.4 g (61%) of colorless ethyl ester of boiling point 75° to 80° C./0.2–0.3 mm Hg which, according to the NMR spectrum (CDCl$_3$) was identical to a specimen prepared from 2,2-dimethyl-3-(β,β-dichlorovinyl)-cyclopropanecarboxylic acid via the acid chloride.

EXAMPLE 7a

Preparation of 2,2-dimethyl-3-(α,β,β-trichlorovinyl)-cyclobutanone

A solution of 150 ml of dry methylene chloride and 45.0 g (0.336 mol) of 1-chloro-1-dimethylamino-2-methyl-1-propene was added dropwise to a mixture of 53.0 g (0.336 mol) of 1,1,2-trichlorobuta-1,3-diene, 55.0 g (0.405 mol) of anhydrous zinc chloride and 250 ml of dry methylene chloride; the temperature of the solution rose from 20° C. initially to 35° C. The solution was stirred for 5 hours under reflux and allowed to cool to 20° C.; 850 ml of 1N NaOH were added dropwise at 20° C., while stirring. After adding 800 ml of carbon tetrachloride, the phases were separated and the organic phase was washed with water until it gave a neutral reaction and clarified over anhydrous sodium sulphate. Evaporation of the solvent gave 68.1 g (89%) of 2,2-dimethyl-3-(α,β,β-trichlorovinyl)-cyclobutanone as a yellowish oil.

Boiling point 118°–121° C./12 mm Hg; $n_D^{20}$ = 1.512.
IR (CCl$_4$) 1,790 cm$^{-1}$ (CO).
NMR (CDCl$_3$) δ 1.17 s (3H), 1.39 s (3H) and 3.30–3.80 ppm m (3H).
C$_8$H$_9$Cl$_3$O: (227.5); calculated C 42.23, H 3.99, Cl 46.75; found 42.5, 3.92, 46.2.

EXAMPLE 7b

Preparation of 2,2-dimethyl-3-(α,β,β-trichlorovinyl)-cyclobutanone (variation using a Lewis acid)

In each case, 0.3 mol of the Lewis acid indicated below was suspended in 160 ml of methylene chloride and a solution of 36.8 g (0.275 mol) of 1-chloro-1-dimethylamino-2-methyl-1-propene in 40 ml of methylene chloride was added in the course of 30 minutes, while cooling (15° C.) and stirring. The mixture was heated to reflux for 5 hours, 300 ml of water were added, whilst cooling with ice, and the mixture was stirred for 15 hours at 20° C. Separation of the phases and washing of the organic phase with water until neutral, drying over sodium sulphate and concentrating in vacuo gave the crude ketone which, in each case, was subjected to fractional distillation.

The yields indicated below were obtained:

| Lewis acid | Yield of ketone |
| --- | --- |
| Zinc chloride | 91.5% |
| Aluminum chloride | 66% |
| Tin(II) chloride | 61% |
| Titanium(IV) chloride | 71% |
| Tin(IV) chloride | 73% |

EXAMPLE 8

Preparation of 2,2,3-trimethyl-3-(α,β,β-trichlorovinyl)-cyclobutanone 58.0 g (0.336 mol) of 1,1,2-trichloro-3-methyl-buta-1,3-diene and 55.0 g (0.405 mol) of anhydrous zinc chloride in 250 ml of dry methylene chloride were heated under reflux with 45.0 g (0.336 mol) of 1-chloro-1-dimethylamino-2-methyl-1-propene in 150 ml of dry methylene chloride for 4 hours and the mixture was then worked up according to Example 2. Fractional distillation gave 47.0 g (58%) of crystalline 2,2,3-trimethyl-3-(α,β,β-trichlorovinyl)-cyclobutanone of melting point 42° to 44° C. (from n-hexane).

IR (CCl$_4$) 1,790 cm$^{-1}$ (CO).
NMR (CDCl$_3$) δ 1.21 s (3H), 1.39 s (3H), 1.45 s (3H), 2.70 d (1H, J=17 Hz) and 3.97 ppm d (1H, J=17 Hz).
C$_9$H$_{11}$Cl$_3$O calculated C 44.76, H 4.59, Cl 44.03; found 44.6, 4.58, 43.7.

The following cyclobutanones were prepared by the process described:

| Example No. | Compound | Physical characteristics |
| --- | --- | --- |
| 9 | 2,2-Diethyl-3-(β,β-dichlorovinyl)-cyclobutanone | $n_D^{20}$ 1.4963 |
| 10 | 2-Ethyl-2-methyl-3-(β,β-dichlorovinyl)-cyclobutanone | $n_D^{20}$ 1.4922 |
| 11 | 2,2-Diethyl-3-(α,β,β-trichlorovinyl)-cyclobutanone | $n_D^{20}$ 1.5153 |
| 12 | 2-Ethyl-2-methyl-3-(α,β,β-trichlorovinyl)-cyclobutanone | $n_D^{20}$ 1.5141 |
| 13 | 3-(α,β,β-trichlorovinyl)-spiro[3,5]-nonan-1-one | $n_D^{20}$ 1.5379 |
| 14 | 3-(β,β-dichlorovinyl)-spiro[3,5]-nonan-1-one | melting point 59–60° C. |
| 15 | 2,2,3-Trimethyl-3-(β,β-dichlorovinyl)-cyclobutanone | boiling point 118–121° C./15 mm Hg |
| 16 | 2,2-Dimethyl-3-(β-chlorovinyl)-cyclobutanone | $n_D^{20}$ 1.4757 |
| 17 | 2,2,4-Trimethyl-3-(β-ethoxycarbonylvinyl)-cyclobutanone | boiling point 86–98° C./0.075 mm Hg |

In addition, the following cyclobutanones could be prepared: 2,2-dimethyl-3-(α-methyl-β,β-dichlorovinyl)-cyclobutanone, 2,2-diethyl-3-(α,β-dichlorovinyl)-cyclobutanone, 2,2-dimethyl-3-(α,β,β-trifluorovinyl)-cyclobutanone, 2,2-dimethyl-3-(α,β-dichlorovinyl)-cyclobutanone, 2,2-dimethyl-3-(β,β-dibromovinyl)-cyclobutanone, 2,2-dimethyl-3-(α-fluoro-β,β-dichlorovinyl)-cyclobutanone, 2,2-dimethyl-3-(β-chlorovinyl)-cyclobutanone, 2,2,3-trimethyl-3-(α,β,β-trifluorovinyl)-cyclobutanone, 2,2-dimethyl-3-(β,β-difluorovinyl)-cyclobutanone, 2-ethyl-2,3-dimethyl-3-(α,β,β-trichlorovinyl)-cyclobutanone, 2,2-diethyl-3-(β,β-dibromovinyl)-cyclobutanone, 2-ethyl-2-methyl-3-(β,β-dibromovinyl)-cyclobutanone, 2-ethyl-2-methyl-3-(α-fluoro-β,β-dichlorovinyl)-cyclobutanone, 2,2-dimethyl-3-(α-ethyl-β,β-dichlorovinyl)-cyclobutanone, 2-ethyl-2,3-dimethyl-3-(β,β-dichlorovinyl)-cyclobutanone, 3-(β,β-dichlorovinyl)-spiro[3,5]-nonan-1-one, 2,2-dimethyl-3-(α,β-dibromovinyl)-cyclobutanone, 3-(β,β-dibromovinyl)-spiro[3,5]-nonan-1-one, 2,2-dimethyl-3-(β-bromo-β-chlorovinyl)-cyclobutanone, 2,2-dimethyl-4-ethyl-3-(β,β-dichlorovinyl)-cyclobutanone, 2,2,4-trimethyl-3-(α,β-dibromovinyl)-cyclobutanone, 2,2-dimethyl-4-n-butyl-3-(β,β-dichlorovinyl)-cyclobutanone and 2-methyl-3-(α,β,β-trichlorovinyl)-cyclobutanone.

EXAMPLE 18

Preparation of 4-bromo-2,2-dimethyl-3-(α,β,β-trichlorovinyl)-cyclobutanone

A solution of 42.5 g (0.186 mol) of 2,2-dimethyl-3-(α,β,β-trichlorovinyl)-cyclobutanone, 31.1 g (0.194 mol) of bromine and 150 ml of 1% strength hydrobromic acid in carbon tetrachloride was allowed to stand at 20° to 25° C. for 15 hours. The hydrogen bromide formed was then driven out with nitrogen and the solution was washed with water until it gave a neutral reaction, clarified over anhydrous sodium sulphate and concentrated. This gave 56.7 g (quantitative) of crystalline 4-bromo-2,2-dimethyl-3-(α,β,β-trichlorovinyl)-cyclobutanone which, according to the NMR spectrum, contained only one of the two isomeric bromoketones.

Melting point 76° to 77° C. (from n-hexane).
IR (CCl$_4$) 1,800 cm$^{-1}$ (CO).
NMR (CDCl$_3$) δ 1.25 s (3H), 1.50 s (3H), 3.74 d (1H, J=8.5 Hz) and 5.46 ppm d (1H, J=8.5 Hz).
C$_8$H$_8$BrCl$_3$O: (306.4); calculated C 31.36, H 2.63, Br 26.1, Cl 34.7; found 31.3, 2.70, 25.7, 34.3.

EXAMPLE 19

Preparation of 4-bromo-2,2,4-trimethyl-3-(β,β-dichlorovinyl)-cyclobutanone 2.08 g (0.01 mol) of 2,2,4-trimethyl-3-(β,β-dichlorovinyl)-cyclobutanone (mixture of isomers) in 8 ml of glacial acetic acid were reacted with 1.6 g (0.01 mol) of bromine according to Example 3. This gave, after working up, 2.65 g of a yellowish oil, the NMR spectrum (CDCl$_3$) of which showed the following signals: δ 1.20 s (3H), 1.34 s (3H), 1.39 s (3H), 1.52 s (3H), 1.78 s (3H), 1.92 s (3H), 3.08 d (1H, J=8.5 Hz), 3.68 d (1H, J=9 Hz), 6.00 d (1H, J=9 Hz) and 6.26 ppm d (1H, J=8.5 Hz).

From the comparison of the intensities of the signals at δ 1.92/1.78, 3.08/3.68 and 6.26/6.00 ppm, an isomer ratio of the 4-bromo-2,2,4-trimethyl-3-(β,β-dichlorovinyl)-cyclobutanones of about 3:2 was calculated.

EXAMPLE 20

Preparation of 4-bromo-2,2,3-trimethyl-3-(α,β,β-trichlorovinyl)-cyclobutanone 23.0 g (0.144 mol) of bromine were added to a solution of 33.6 g (0.14 mol) of 2,2,3-trimethyl-3-(α,β,β-trichlorovinyl)-cyclobutanone in 120 ml of carbon tetrachloride, which contained 1% of hydrobromic acid, at 20° C. After standing for 20 hours at 20° C., the solution was decolorized. It was worked up as described for Example 18 and 40.2 g (89%) of almost homogeneous crystalline 4-bromo-2,2,3-trimethyl-3-(α,β,β-trichlorovinyl)-cyclobutanone were isolated.

Melting point 81° to 82° C. (from n-hexane). According to the evidence of the NMR spectrum of the crude product, only one of the isomeric bromoketones was present.

IR (CCl$_4$) 1,800 cm$^{-1}$ (CO).
NMR (CDCl$_3$) δ 1.31 s (3H), 1.47 s (6H) and 5.82 ppm s (1H).
C$_9$H$_{10}$BrCl$_3$O: (320.5); calculated C 33.73, H 3.15, Br 24.9, Cl 33.2; found 34.0, 3.22, 24.4, 32.9.

The following α-bromocyclobutanones were prepared by the process described:

| Example No. | Compound | Physical characteristics |
|---|---|---|
| 21 | 4-Bromo-2,2-diethyl-3-(α,β,β-trichlorovinyl)-cyclobutanone | IR(CCl$_4$) 1790 cm$^{-1}$ |
| 22 | 4-Bromo-2-ethyl-2-methyl-3-(α, β,β-trichlorovinyl)-cyclobutanone | IR(CCl$_4$) 1790 cm$^{-1}$ |
| 23 | 2-Bromo-3-(α,β,β-trichlorovinyl)-spiro[3,5]nonan-1-one | melting point 76–77° C. |

In addition, the following cyclobutanones could be brominated in the 4-position: 2,2-dimethyl-3-(α-methyl-β,β-dichloro-vinyl)-cyclobutanone, 2,2-diethyl-3-(α,β-dichlorovinyl)-cyclobutanone, 2,2-dimethyl-3-(α,β,β-trifluorovinyl)-cyclobutanone, 2,2-dimethyl-3-(α,β-dichlorovinyl)-cyclobutanone, 2,2-dimethyl-3-(β,β-dibromovinyl)-cyclobutanone, 2,2-dimethyl-3-(α-fluoro-β,β-dichlorovinyl)-cyclobutanone, 2,2-dimethyl-3-(β-chlorovinyl)-cyclobutanone, 2,2,3-trimethyl-3-(α,β,β-trifluorovinyl)-cyclobutanone, 2,2-dimethyl-3-(β,β-difluorovinyl)-cyclobutanone, 2-ethyl-2-methyl-3-(β,β-dichlorovinyl)-cyclobutanone, 2-ethyl-2,3-dimethyl-3-(α,β,β-trichlorovinyl)-cyclobutanone, 2,2-diethyl-3-(β,β-dibromovinyl)-cyclobutanone, 2-ethyl-2-methyl-3-(β,β-dibromovinyl)-cyclobutanone, 2-ethyl-2-methyl-3-(α-fluoro-β,β-dichlorovinyl)-cyclobutanone, 2,2-dimethyl-3-(α-ethyl-β,β-dichlorovinyl)-cyclobutanone, 2-ethyl-2,3-dimethyl-3-(β,β-dichlorovinyl)-cyclobutanone, 2,2-dimethyl-3-(α,β-dibromovinyl)-cyclobutanone, 2,2-dimethyl-3-(β-bromo-β-chlorovinyl)-cyclobutanone, 2,2-dimethyl-4-ethyl-3-(β,β-dichlorovinyl)-cyclobutanone, 2,2,4-trimethyl-3-(α,β-dibromovinyl)-cyclobutanone, 2,2-dimethyl-4-n-butyl-3-(β,β-dichlorovinyl)-cyclobutanone, 2-methyl-3-(α,β,β-trichlorovinyl)-cyclobutanone, 2,2-di-n-propyl-3-(α,β,β-trichlorovinyl)-cyclobutanone, 2-hexyl-3-(β,β-dichlorovinyl)-cyclobutanone, 2-methyl-2-butyl-3-(α,β,β-trichlorovinyl)-cyclobutanone, 2,2-dimethyl-3-(α-cyano-β,β-dichlorovinyl)-cyclobutanone, 2,2-dimethyl-3-n-butyl-3-(β,β-dichlorovinyl)-cyclobutanone, 2,2-dimethyl-3-(β-chloro-β-methoxycarbonylvinyl)-cyclobutanone, 2,2-dimethyl-3-(β,β-dicyanovinyl)-cyclobutanone, 2,3-dimethyl-3-(β,β-dibromovinyl)-cyclobutanone, 2,2-dimethyl-3-(β,β-dibromovinyl)-4-n-butyl-cyclobutanone, 2,2-di-n-butyl-3-methyl-3-(α-chloro-β-cyanovinyl)-cyclobutanone, 2,2-dimethyl-3-(α-methylsulphonylvinyl)-cyclobutanone, 2,2-diethyl-3-(β,β-dichlorovinyl)-4-cyclohexyl-cyclobutanone, 2-methyl-2-phenyl-3-(β,β-dichlorovinyl)-cyclobutanone, 2,2-dimethyl-3-(β-chloro-β-phenylvinyl)-cyclobutanone, 2,2-dimethyl-3-(β,β-bis-(trifluoromethyl)-vinyl)-cyclobutanone, 2,2-dimethyl-3-(α,β,β-trichlorovinyl)-4-benzyl-cyclobutanone and 2-cyclohexyl-3-(β,β-dichlorovinyl)-cyclobutanone; and the following spiro-cyclic cyclobutanones could be brominated in the 2-position: 3-(β,β-dichlorovinyl)-spiro[3,5]nonan-1-one, 3-(β,β-dibromovinyl)-spiro[5,3]nonan-1-one, 3-(β,β-dichlorovinyl)-spiro[4,3]octan-1-one, 3-(β,β-dichlorovinyl)-2-methyl-spiro[5,3]nonan-1-one, 3-(α,β-dichlorovinyl)-spiro[5,3]nonan-1-one and 3-(α,β,β-trifluorovinyl)-spiro[3,5]nonan-1-one.

EXAMPLE 24

Preparation of 4-chloro-2,2-dimethyl-3-(α,β,β-trichlorovinyl)-cyclobutanone

A total of 17 ml of previously condensed chlorine (about 0.3 mol) were passed into a solution of 55.9 g (0.246 mol) of 2,2-dimethyl-3-(α,β,β-trichlorovinyl)-cyclobutanone in 200 ml of carbon tetrachloride at 20° C., while stirring. After allowing to stand (15 hours), hydrogen chloride and unreacted chlorine were removed by passing nitrogen into the reaction solution and the mixture was then extracted with water, 5% strength sodium thiosulphate solution and again with water. Drying the organic phase over sodium sulphate and concentration gave 63.95 g of a crystalline product which was crystallized from 100 ml of n-hexane. Melting point 77°–78° C.

$C_8H_8Cl_4O$: (262.0); Calculated C 36.68, H 3.08, Cl 54.14; Found 36.5, 2.87, 53.8.

IR($CCl_4$): 1810 cm$^{-1}$.

NMR (CDCl$_3$): δ = 1.25 s (3H), 1.48 s (3H), 3.65 and 5.36 ppm AB quartet (J = 8.5 Hz, 2H).

EXAMPLE 25

Preparation of 2,2-dimethyl-3-(α,β,β-trichlorovinyl)-cyclopropanecarboxylic acid 58.6 g (0.26 mol) of crude 2,2-dimethyl-3-(α,β,β-trichlorovinyl)-cyclobutanone in 330 ml of carbon tetrachloride, which contained 1% of hydrogen bromide, were allowed to stand at 20° C. with 41.5 g (0.26 mol) of bromine for 15 hours. The hydrogen bromide formed was substantially driven out from the decolorized solution and 570 ml of 1.3N NaOH were added to the solution at 20° C. in the course of 2 hours, while stirring. After 6 hours, the organic phase was separated off. Acidification of the aqueous alkaline phase with concentrated hydrochloric acid, while cooling, gave, after extraction by shaking with ether, washing until neutral and clarification of the ether phase over anhydrous sodium sulphate, 56.6 g (89.3%) of crystalline 2,2-dimethyl-3-(α,β,β-trichlorovinyl)-cyclopropanecarboxylic acid which, according to the NMR spectrum and within the accuracy of measurement, contained only one of the two isomers. Melting point 90° to 93° C. (from petroleum ether).

EXAMPLE 26

Preparation of 1,2,2-trimethyl-3-(β,β-dichlorovinyl)-cyclopropanecarboxylic acid The crude 4-bromo-2,2,4-trimethyl-3-(β,β-dichlorovinyl)-cyclobutanone (2.55 g) obtained according to Example 19 was suspended in 25 ml of 2N NaOH and the suspension was stirred at 20° C. for 6 hours. The mixture was worked up as described for Example 5 to give 1.93 g (86%) (relative to 0.01 mol of 2,2,4-trimethyl-3-(β,β-dichlorovinyl)-cyclobutanone) of crystalline 1,2,2-trimethyl-3-(β,β-dichlorovinyl)-cyclopropanecarboxylic acid as a mixture of isomers of melting point 87° to 95° C.

Fractional crystallization gave the homongenous isomers.

Isomer A

NMR (CDCl$_3$) δ 1.11 s (3H), 1.23 s (3H), 1.30 s (3H), 2.39 d (1H), J = 7.5 Hz), 5.63 d (1H, J = 7.5 Hz) and 9.80 ppm s (1H).

Isomer B

NMR (CDCl$_3$) δ 1.30 s (6H), 1.45 s (3H), 1.68 d (1H, J = 8.5 Hz), 6.26 s (1H, J = 8.4 Hz) and 9.60 ppm s (1H).

EXAMPLE 27

Preparation of 2,2,3-trimethyl-3-(α,β,β-trichlorovinyl)-cyclopropanecarboxylic acid A suspension of 21.16 g (0.066 mol) of 4-bromo-2,2,3-trimethyl-3-(α,β,β-trichlorovinyl)-cyclobutanone in 150 ml of 1N NaOH was stirred for 10 hours at 20° C. The mixture was worked up as indicated for Example 5 to give 1.58 g of neutral products (unreacted bromoketone) and 13.73 g (87%) of crystalline 2,2,3-trimethyl-3-(α,β,β-trichlorovinyl)-cyclopropanecarboxylic acid of melting point 152° to 153° C. (from benzene/n-hexane).

IR (CCl$_4$) 1700 cm$^{-1}$.

NMR (CDCl$_3$) δ 1.30 s (6H), 1.50 s (3H), 1.79 s and 1.95 s (1H) and 9.8 ppm s (1H).

$C_9H_{11}Cl_3O_2$: (257.6); Calculated C 41.97, H 4.31, Cl 41.30; Found 42.2, 4.33, 41.1.

EXAMPLE 28

Preparation of 2,2-dimethyl-3-(α,β,β-trichlorovinyl)-cyclopropanecarboxylic acid A suspension of 30.6 g (0.1 mol) of 4-bromo-2,2-dimethyl-3-(α,β,β-trichlorovinyl)-cyclobutanone in 150 ml of 2N NaOH was stirred at 20° to 25° C. for 10 hours. The homogeneous solution was extracted with dibutyl ether in order to remove neutral products, acidified with 10% strength aqueous sodium chloride, while cooling, and 2,2-dimethyl-3-(α,β,β-trichlorovinyl)-cyclopropanecarboxylic acid, which was obtained in crystalline form, was filtered off and washed until neutral.

Yield 23.8 g (about 100%).

IR (CCl$_4$) 1,705 cm$^{-1}$ (CO).

NMR (C$_6$D$_6$) δ 0.86 s (1H), 1.16 s (1H), 1.99 d (1H, J = 5.5 Hz), 2.34 d (1H, J = 5.5 Hz) and 12.1 ppm s (1H).

$C_8H_9Cl_3O_2$ calculated C 39.46, H 3.73, Cl 43.68; found 39.3, 3.81, 43.4.

The following cyclopropane-carboxylic acids were prepared by the process described:

| Example No. | Compound | Physical characteristics |
|---|---|---|
| 29 | 2,2-Diethyl-3-(α,β,β-trichlorovinyl)-cyclopropane-cartoxylic acid | melting point 117–118° C. |
| 30 | 2-Ethyl-2-methyl-3-(α,β,β-trichlorovinyl)-cyclopropanecarboxylic acid | melting point 50–77° C. |
| 31 | 2-(α,β,β-trichlorovinyl)-spiro[2,5]octane-1-carboxylic acid | melting point 129–131° C. |

In addition, the following cyclopropanecarboxylic acids could be prepared: 2,2-dimethyl-3-(α,β,β-trifluorovinyl)-cyclopropanecarboxylic acid, 2,2-diethyl-3-(β,β-dichlorovinyl)-cyclopropanecarboxylic acid, 2,2,3-trimethyl-3-(β,β-dichlorovinyl)-cyclopropanecarboxylic acid, 2,2-dimethyl-3-(β,β-dibromovinyl)-cyclopropanecarboxylic acid, 2,2-dimethyl-3-(α,β-dibromovinyl)-cyclopropanecarboxylic acid, 2,2-dimethyl-3-(α-cyano-β,β-dichlorovinyl)-cyclopropanecarboxylic acid, 1-ethyl-2,2-dimethyl-3-(β,β-dichlorovinyl)-cyclopropanecarboxylic acid, 2-(β,β-dichlorovinyl)-spiro[2,5]octane-1-carboxylic acid, 2,2-dimethyl-3-(β,β-dibromovinyl)-cyclopropanecarboxylic acid, 2,2-dimethyl-3-(α-chloro-β,β-difluorovinyl)-cyclopropanecarboxylic acid, 2-(β,β-dichlorovinyl-spiro[2,4]-heptane-1-carboxylic acid and 2-methyl-3-(α,β,β-trichlorovinyl)-cyclopropanecarboxylic acid.

EXAMPLE 32

Preparation of
2,2-dimethyl-3-($\alpha,\beta,\beta$-trichlorovinyl)-cyclopropanecarboxylic acid A suspension of 40.63 g (0.154 mol) of 4-chloro-2,2-dimethyl-3-($\alpha,\beta,\beta$-trichlorovinyl)-cyclobutanone in 500 ml of 1N NaOH (0.5 mol) was stirred for 15 hours at 20°–25° C. Neutral products were separated off by extraction with ether and the alkaline solution was acidified with hydrochloric acid, while cooling. Extraction with ether, washing with water until neutral, drying over sodium sulphate and evaporation in vacuo gave 23.1 g (62%) of colorless crystals of 2,2-dimethyl-3-($\alpha,\beta,\beta$-trichlorovinyl)-cyclopropanecarboxylic acid of melting point 89°–91° C.

EXAMPLE 33

Preparation of
2,2-dimethyl-3-(bromovinyl)-cyclopropanecarboxylic acid ethyl ester 32.0 g (0.2 mol) of bromine in 40 ml of carbon tetrachloride were added dropwise to a solution of 12.4 g (0.1 mol) of 2,2-dimethyl-3-vinylcyclobutanone in 100 ml of carbon tetrachloride at 10° C. in the course of 2 hours. The mixture was subsequently stirred for 1 hour, hydrogen bromide formed was dispelled with nitrogen and the solution was washed successively with water, 1% strength aqueous sodium thiosulphate solution and water, clarified over anhydrous sodium sulphate and concentrated in vacuo. Yield: 31.83 g, IR (CCl$_4$): 1805 cm$^{-1}$.

C$_8$H$_{11}$Br$_3$O: (363); Calculated Br 66.2%; Found 65.3%.

A solution of 31.0 g of 2,2-dimethyl-3-($\alpha,\beta$-dibromoethyl)-4-bromo-cyclobutanone in 40 ml of absolute ethanol was added dropwise to a solution of 4.6 g (0.2 mol) of sodium in 70 ml of absolute ethanol at 0°–5° and the mixture was subsequentlfy stirred for 1 hour at 40°–50°. Ethanolic hydrochloric acid was added to the cooled solution in order to neutralize the excess base, the sodium bromide which had separated out was filtered off and the filtrate was concentrated. Fractional distillation gave two main fractions:

(A) 7.55 g of a colorless oil of boiling point 53°–58° C./0.2–0.3 mm Hg

IR (CCl$_4$): 1725 cm$^{-1}$ (ester-carbonyl).

NMR (CDCl$_3$): signals at, inter alia $\delta$ 5.52 (2 vinyl protons), 4.15 (2 methylene protons of the ethyl group), 1.30 (3 methyl protons), 1.20 (3 methyl protons) and 1.26 ppm (3 methyl protons of the ethyl group).

C$_{10}$H$_{15}$BrO$_2$: (247.1); Calculated C 48.59, H 6.12, Br 32.34; Found 48.6, 5.83, 32.2. (Calculated for 2,2-dimethyl-3-(bromovinyl)-cyclopropanecarboxylic acid ethyl ester)

(B) 5.2 g of a colorless oil of boiling point 63°–70° C./0.1–0.3 mmg Hg.

According to the analytical data (IR, NMR and elementary analysis), this was a mixture of isomeric 2,2-dimethyl-3-(bromovinyl)-cyclopropanecarboxylic acid ethyl esters.

EXAMPLE 34

Preparation of
2-($\alpha,\beta,\beta$-trichlorovinyl)-spiro[2,5]octane-1-carboxylic acid ethyl ester 16.1 g (0.0463 mol) of 2-bromo-3-($\alpha,\beta,\beta$-trichlorovinyl)-spiro[3,5]nonan-1-one in 80 ml of ether were added dropwise to a solution of 1.07 g (0.0463 mol) of sodium in 20 ml of ethanol in the course of 30 minutes at 15°–20° C., while stirring and cooling. After heating under reflux for one hour, the reaction mixture was poured onto ice and extracted with ether. Washing the organic phase with saturated sodium bicarbonate solution and water, drying over sodium sulphate and subsequent concentration gave 13.3 g of oil which was subjected to fractional distillation. This gave 11.3 g (78%) of ethyl ester of boiling point 116° C./0.15 mm Hg, n$_D^{20}$ of 1.5125.

C$_{13}$H$_{17}$Cl$_3$O$_2$: (311.7); Calculated C 50.1, H 5.5, Cl 34.1; Found 50.1, 5.3, 33.9.

IR (CCl$_4$): 1735 cm$^{-1}$ (ester-carbonyl).

NMR (CDCl$_3$): $\delta$=1.28 t (3H J=7.5 Hz), 1.3–2.0 m (10H), 2.05 and 2.48, AB-quartet (J=5.5 Hz, 2H) and 4.18 ppm q (2H J=7.5 Hz).

EXAMPLE 35

Preparation of
2,2-dimethyl-3-($\alpha,\beta,\beta$-trichlorovinyl)-cyclopropanecarboxylic acid ethyl ester 7.66 g (0.025 mol) of 4-bromo-2,2-dimethyl-3-($\alpha,\beta,\beta$-trichlorovinyl)-cyclobutanone in 40 ml of dry ether were added dropwise to a suspension of 1.7 g (0.025 mol) of sodium ethylate in 9 ml of anhydrous ethanol at 15° C. The mixture was subsequently stirred for 1 hour at 15° C. and poured onto ice/1N HCl. The phases were separated, the aqueous phase was washed twice with ether and the combined ether extracts were then washed with aqueous sodium bicarbonate solution and water until they gave a neutral reaction. Drying over anhydrous sodium sulphate gave 5.94 g (87%) of 2,2-dimethyl-3-($\alpha,\beta,\beta$-trichlorovinyl)-cyclopropanecarboxylic acid ethyl ester.

Boiling point 73° to 74° C./0.2 mm Hg; n$_D^{20}$=1.4920.
IR (CCl$_4$) 1,726 cm$^{-1}$ (CO).

NMR (CDCl$_3$) $\delta$ 1.20 s (3H), 1.30 t (3H, J=7.5 Hz), 1.33 s (3H), 2.04 d (1H, J=6 Hz), 2.45 d (1H, J=6 Hz) and 4.19 ppm q (2H, J=7.5 Hz).

0.9 g of 2,2-dimethyl-3-($\alpha,\beta,\beta$-trichlorovinyl)-cyclopropanecarboxylic acid were obtained from the bicarbonate extract by acidification with 10% strength hydrochloric acid and extraction with ether.

C$_{10}$H$_{13}$Cl$_3$O$_2$: (271.6); calculated C 44.23, H 4.83, Cl 39.17; found 43.9, 5.09, 38.6.

The following esters could be prepared by the above process: 2,2-dimethyl-3-($\beta,\beta$-dibromovinyl)-cyclopropanecarboxylic acid ethyl ester, 2,2-dimethyl-3-($\alpha,\beta,\beta$-trifluorovinyl)-cyclopropanecarboxylic acid methyl ester, 2,2-diethyl-3-($\alpha,\beta,\beta$-trichlorovinyl)-cyclopropanecarboxylic acid ethyl ester, 2,2-diethyl-3-($\beta,\beta$-dichlorovinyl)-cyclopropanecarboxylic acid ethyl ester, 2,2,3-trimethyl-3-($\beta,\beta$-dichlorovinyl)-cyclopropanecarboxylic acid ethyl ester, 1,2,2-trimethyl-3-($\beta,\beta$-dichlorovinyl)-cyclopropanecarboxylic acid ethyl ester, 2,2-dimethyl-3-($\beta,\beta$-dichlorovinyl)-cyclopropanecarboxylic acid methyl ester, 2-($\beta,\beta$-dichlorovinyl)-spiro[2,5]octane-1-carboxylic acid ethyl ester and 2-methyl-2-ethyl-3-(β,β-dichlorovinyl)-cyclopropanecarboxylic acid n-propyl ester.

EXAMPLE 36

Preparation of
2,2-dimethyl-3-(α,β,β-trichlorovinyl)-cyclopropanecarboxylic acid m-phenoxybenzyl ester A solution of 12.2 g (0.05 mol) of 2,2-dimethyl-3-(α,β,β-trichlorovinyl)-cyclopropanecarboxylic acid and 6.85 g (0.0575 mol) of thionyl chloride in 50 ml of dry benzene was heated under reflux for 1.5 hours. Excess thionyl chloride and gaseous reaction products were removed under a waterpump vacuum. 20 ml of dry benzene, 15 ml of dry pyridine and 8.0 g (0.04 mol) of m-phenoxy-benzyl alcohol were added successively to the resulting residue. After standing for 15 hours at 20° C., the reaction mixture was poured onto ice, with the addition of 100 ml of benzene, and the benzene phase was separated off and washed successively with dilute hydrochloric acid, water, 2N $Na_2CO_3$ and water. Drying over sodium sulphate and evaporation gave 16.5 g of a colorless oil which, in order to separate off unreacted m-phenoxybenzyl alcohol, was dissolved in 100 ml of n-hexane and filtered through 50 g of silica gel. Distillation in a bulb tube gave 14.7 g of 2,2-dimethyl-3-(α,β,β-trichlorovinyl)-cyclopropanecarboxylic acid m-phenoxybenzyl ester as a colorless oil of boiling point 190° to 195° C./0.01 mm Hg. The ester proved to be homogeneous in analysis by thin-layer chromatography.

IR ($CCl_4$) 1,735 $cm^{-1}$ (CO).

NMR ($CDCl_3$) δ 1.18 s (3H), 1.27 s (3H), 2.07 d (1H, J=6 Hz), 2.44 d (1H, J=6 Hz), 5.12 s (2H) and 6.90–7.50 ppm m (9H).

$C_{21}H_{19}Cl_3O_3$: (425.5); calculated C 59.1, H 4.46, Cl 25.0; found 59.2, 4.70, 25.1.

The aqueous phase which resulted during the working up was acidified with dilute hydrochloric acid and 1.45 g of 2,2-dimethyl-3-(α,β,β-trichlorovinyl)-cyclopropanecarboxylic acid were recovered by extraction with ether.

EXAMPLE 37

Preparation of
2,2-dimethyl-3-(α-bromo-β,β-dichlorovinyl)-cyclopropanecarboxylic acid ethyl ester A solution of 3.2 g (0.02 mol) of bromine in 5 ml of carbon tetrachloride was added dropwise to 1.95 g (0.01 mol) of 2,2-dimethyl-3-(β,β-dichlorovinyl)-cyclobutanone in 5 ml of carbon tetrachloride, which contained 5% of hydrogen bromide, at 25° C. The mixture was subsequently stirred for 6 hours, hydrogen bromide which had formed was removed by passing a dry stream of nitrogen through and the reaction solution was concentrated. The residue, the NMR spectrum ($CDCl_3$) of which, in agreement with the bromination of the dichlorovinyl group by the second mol equivalent of bromine, showed no signal for a vinyl proton, was dissolved in 30 ml of ether and the solution was added dropwise to a solution of 0.7 g (about 0.03 mol) of sodium in 30 ml of absolute ethanol at 20° to 25° C. The mixture was allowed to react further for 1 hour at 60° C. and was worked up as described for Example 6. This gave 2.19 g (69%) of 2,2-dimethyl-3-(α-bromo-β,β-dichlorovinyl)-cyclopropanecarboxylic acid ethyl ester of boiling point 85° to 90° C./0.3 mm Hg.

Calculated Br 25.3; Found 25.0.

EXAMPLE 38

Preparation of
2,2-dimethyl-3-(α,β,β-trichlorovinyl)-cyclopropanecarboxylic acid m-phenoxybenzyl ester 5.0 g (0.025 mol) of m-phenoxybenzyl alcohol were added to a solution of 0.520 g (0.0226 mol) of sodium in 10 ml of absolute ethanol, under nitrogen, and the ethanol was distilled off in vacuo. Two 50 ml portions of absolute toluene were added to the residue and the mixture was evaporated to dryness in vacuo. 5.75 g (0.019 mol) of 4-bromo-2,2-dimethyl-3-(α,β,β-trichlorovinyl)-cyclobutanone in 20 ml of abslute toluene were added dropwise to a suspension of the resulting solid residue in 30 ml of absolute toluene at 15° C. and the mixture was subsequently stirred for 6 hours at 20° C. According to analysis by thin layer chromatography, complete conversion had taken place. The reaction mixture was added to ice/dilute hydrochloric acid and the organic phase was separated off, washed until it gave a neutral reaction and filtered over 100 g of silica gel.

Yield: 5.12 g (60%) of 2,2-dimethyl-3-(α,β,β-trichlorovinyl)-cyclopropanecarboxylic acid m-phenoxybenzyl ester.

According to analysis by thin layer chromatography and the NMR spectrum, the product was identical to the product obtained in Example 36.

EXAMPLE 39

Preparation of
2,2,3-trimethyl-3-(α,β,β-trichlorovinyl)-cyclopropanecarboxylic acid m-phenoxybenzyl ester 10.3 g of 2,2,3-trimethyl-3-(β,β,β-trichlorovinyl)-cyclopropanecarboxylic acid (0.04 mol) were reacted, according to Example 36, with 5.8 g (0.048 mol) of thionyl chloride in 50 ml of dry benzene to give the acid chloride. 25 ml of benzene, 15 ml of pyridine and 8.0 g (0.04 mol) of m-phenoxybenzyl alcohol were added successively to the crude acid chloride. After standing for 10 hours at 20° C., the mixture was worked up according to Example 36 to give 16.2 g of crude ester. Chromatography to silica gel and fractional distillation gave 13.1 g (74%) of 2,2,3-trimethyl-3-(α,β,β-trichlorovinyl)-cyclopropanecarboxylic acid m-phenoxybenzyl ester as a colorless oil of boiling point 200° to 210° C./0.1–0.15 mm Hg.

IR ($CCl_4$) 1,730 $cm^{-1}$ (CO).

NMR ($CDCl_3$) δ 1.24 s (3H), 1.29 s (3H), 1.45 s (3H), 1.87 s and 1.99 s (1H), 5.10 s (2H) and 6.80–7.50 ppmm (9H).

$C_{22}H_{21}Cl_3O_3$ Calculated C 60.08, H 4.81, C 24.19; Found 60.4, 4.65, 24.0.

It will be appreciated that the instant specification and examples are set forth by way of illustration and not limitation, and that various modifications and changes may be made without departing from the spirit and scope of the present invention.

What is claimed is:

1. A process for the preparation of an α-halogenocyclobutanone of the formula

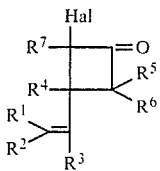

in which
R$^1$, R$^2$ and R$^3$ each independently is hydrogen, halogen, CN, optionally substituted alkyl, or alkenyl, aralkyl, aryl, alkoxycarbonyl, alkylsulphonyl, arylsulphonyl, acyloxy or dialkylaminocarbonyl, at least one of the radicals R$^1$, R$^2$ and R$^3$ containing hydrogen,
R$^4$, R$^5$, R$^6$ and R$^7$ each independently is hydrogen, optionally substituted alkyl or alkenyl, halogen, CN, aralkyl or aryl, or any of the pairs R$^1$ and R$^2$, R$^2$ and R$^3$, R$^1$ and R$^4$, R$^4$ and R$^5$, R$^4$ and R$^7$ and R$^5$ and R$^6$, conjointly with the adjacent carbon atoms or atoms from a carbocyclic ring with up to 8 ring carbon atoms, and
Hal is halogen, comprising to produce a cyclobutanone of the formula

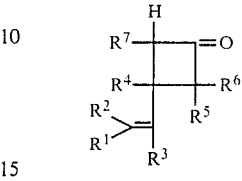

and brominating the cyclobutanone.

* * * * *

UNITED STATES PATENT AND TRADEMARK OFFICE
CERTIFICATE OF CORRECTION

PATENT NO. : 4,529,813

DATED : July 16, 1985

INVENTOR(S) : Hans-Georg Heine et al.

It is certified that error appears in the above-identified patent and that said Letters Patent is hereby corrected as shown below:

| | |
|---|---|
| 1st page, after "[22] Filed: March 14, 1980" | Insert --[30] <u>Foreign Application Priority Data</u><br>August 26, 1976 [DE] Fed. Rep. of Germany ... 26 38 356 -- |
| Col. 3, line 50; Col. 5 lines 38 and 44 | Delete "and" first occurrence and insert --to-- |
| Col. 15, line 42 | Delete "of" and insert --off-- |
| Col. 27, line 46 | Delete "tetrafluoroboratain" and insert --tetrafluoroboratein-- |
| Col. 38, line 15 | Delete "abslute" and insert --absolute-- |

Signed and Sealed this

Seventeenth Day of December 1985

[SEAL]

Attest:

DONALD J. QUIGG

Attesting Officer

*Commissioner of Patents and Trademarks*

UNITED STATES PATENT AND TRADEMARK OFFICE
CERTIFICATE OF CORRECTION

PATENT NO. : 4,529,813
DATED : July 16, 1985
INVENTOR(S) : Hans-Georg Heine, et al.

It is certified that error appears in the above-identified patent and that said Letters Patent is hereby corrected as shown below:

Title Page, under "Related U.S. Application Data"

After "Aug. 24, 1977," delete "abandoned" and insert --now U.S. Patent No. 4,291,176 issued September 22, 1981--

Signed and Sealed this

Eighteenth Day of February 1986

[SEAL]

Attest:

Attesting Officer

DONALD J. QUIGG

Commissioner of Patents and Trademarks